(12) United States Patent
Mukherjee

(10) Patent No.: US 7,115,728 B1
(45) Date of Patent: Oct. 3, 2006

(54) HUMAN PEROXISOME PROLIFERATOR ACTIVATED RECEPTOR γ

(75) Inventor: Ranjan Mukherjee, San Diego, CA (US)

(73) Assignee: Ligand Pharmaceutical Incorporated, San Diego, CA (US)

( * ) Notice: Subject to any disclaimer, the term of this patent is extended or adjusted under 35 U.S.C. 154(b) by 0 days.

(21) Appl. No.: 08/484,487

(22) Filed: Jun. 7, 1995

Related U.S. Application Data

(63) Continuation-in-part of application No. 08/380,051, filed on Jan. 30, 1995, now abandoned.

(51) Int. Cl.
*C12N 15/11* (2006.01)

(52) U.S. Cl. .................................... 536/23.5

(58) Field of Classification Search ............ 536/23.5
See application file for complete search history.

(56) References Cited

U.S. PATENT DOCUMENTS

| | | | |
|---|---|---|---|
| 3,845,089 A | 10/1974 | Henrick | 554/220 |
| 3,884,758 A | 5/1975 | Green | 435/34 |
| 4,105,681 A | 8/1978 | Bollag et al. | 554/111 |
| 4,193,931 A | 3/1980 | Loeliger | 514/510 |
| 4,215,215 A | 7/1980 | Bollag et al. | 544/176 |
| 4,534,979 A | 8/1985 | Love et al. | 514/529 |
| 4,648,996 A | 3/1987 | Aig et al. | 554/103 |
| 4,783,549 A | 11/1988 | Lang et al. | 560/104 |
| 4,833,254 A | 5/1989 | Berlin et al. | 548/454 |
| 4,879,284 A | 11/1989 | Land et al. | 514/62 |
| 4,892,940 A | 1/1990 | Maignan et al. | 556/55.2 |
| 4,977,276 A | 12/1990 | Berlin et al. | 549/58 |
| 5,130,333 A | 7/1992 | Pan et al. | 514/460 |
| 5,198,567 A | 3/1993 | Lang et al. | 560/56 |
| 5,219,888 A | 6/1993 | Katocs, Jr. et al. | 514/560 |
| 5,264,372 A | 11/1993 | Beaumont et al. | 436/504 |
| 5,304,575 A | 4/1994 | Beck | 514/563 |
| 5,441,971 A | 8/1995 | Sohda et al. | 514/342 |
| 5,508,164 A * | 4/1996 | Kausch et al. | 435/6 |
| 5,512,683 A | 4/1996 | Klaus et al. | 549/9 |
| 5,654,338 A | 8/1997 | Metivier | 514/570 |
| 5,686,596 A | 11/1997 | Mukherjee et al. | 536/23.5 |
| 5,700,836 A | 12/1997 | Klaus et al. | 514/544 |
| 5,705,167 A | 1/1998 | Bernardon et al. | 424/401 |
| 5,726,041 A | 3/1998 | Chrespi et al. | 435/69.1 |
| 5,728,739 A | 3/1998 | Ailhaud et al. | 514/725 |
| 5,763,487 A | 6/1998 | Bernardon | 514/569 |
| 5,861,274 A * | 1/1999 | Evans et al. | 435/69.1 |
| 5,968,908 A | 10/1999 | Epstein et al. | 514/42 |
| 5,972,881 A | 10/1999 | Heyman et al. | 514/3 |
| 5,977,125 A | 11/1999 | Hibi et al. | 514/277 |
| 6,017,924 A | 1/2000 | Edwards et al. | 514/292 |
| 6,028,052 A | 2/2000 | Heyman et al. | 514/3 |
| 6,200,802 B1 | 3/2001 | Greene et al. | 435/325 |
| 6,228,862 B1 | 5/2001 | Heyman et al. | 514/277 |
| 6,294,559 B1 * | 9/2001 | Smith | |
| 6,316,404 B1 | 11/2001 | Heyman et al. | 514/3 |
| 6,521,633 B1 | 2/2003 | Heyman et al. | 514/277 |
| 6,534,516 B1 | 3/2003 | Edwards et al. | 514/285 |
| 6,545,049 B1 | 4/2003 | Canan-Koch et al. | 514/569 |
| 6,815,168 B1 | 11/2004 | Greene et al. | 435/7.1 |
| 2002/0193291 A1 | 12/2002 | Heyman et al. | 514/3 |
| 2004/0019072 A1 | 1/2004 | Canan-Koch et al. | 514/290 |
| 2004/0106135 A1 | 6/2004 | Mukherjee et al. | 435/6 |

FOREIGN PATENT DOCUMENTS

| | | |
|---|---|---|
| DE | 2819213 | 9/1987 |
| EP | 0169571 | 1/1986 |
| EP | 0253393 | 1/1988 |
| EP | 0266992 | 5/1988 |
| EP | 0 305 890 | 3/1989 |
| EP | 0679628 | 11/1995 |
| EP | 0698392 | 2/1996 |
| EP | 0718285 | 6/1996 |
| EP | 0552624 | 7/1997 |
| EP | 0568898 | 4/1998 |
| EP | 0641759 | 12/1998 |
| EP | 0873295 | 4/2003 |
| EP | 1336600 | 8/2003 |
| EP | 0859608 | 2/2004 |
| EP | 1426048 | 6/2004 |
| FR | 2390428 | 12/1978 |
| FR | 2719041 | 10/1995 |
| FR | 2719042 | 10/1995 |
| FR | 2729664 | 7/1996 |
| GB | 2188634 | 10/1987 |
| GB | 2197316 | 5/1988 |
| JP | 05 194 209 A | 8/1993 |
| WO | 83/00930 | 3/1983 |

(Continued)

OTHER PUBLICATIONS

Tontonoz et al. (1994) Genes and Development 8:1224-1234.*

(Continued)

*Primary Examiner*—Michael Pak
(74) *Attorney, Agent, or Firm*—Fish & Richardson P.C.; Stephanie Seidman; Frank J. Miskiel

(57) ABSTRACT

The present invention relates to a novel human peroxisome proliferator activated receptor, hPPARγ. hPPARγ differs from the mouse peroxisome proliferator activated receptor γ in the nucleotide sequence and the amino acid sequence. The invention provides isolated, purified, enriched or recombinant nucleic acid encoding hPPARγ polypeptides and vectors containing thereof, cells transformed with such vectors, and methods of screening for agonists and antagonists of hPPARγ polypeptides. The invention also provides isolated, purified, enriched, or recombinant hPPARγ polypeptides, antibodies having specific binding affinity to hPPARγ polypeptides, and hybridomas producing such antibodies.

36 Claims, 3 Drawing Sheets

FOREIGN PATENT DOCUMENTS

| WO | 89/04489 | 5/1989 |
|---|---|---|
| WO | 91/12258 | 8/1991 |
| WO | 93/09236 | 5/1993 |
| WO | 93/15740 | 8/1993 |
| WO | 93/21146 | 10/1993 |
| WO | 94/12880 | 6/1994 |
| WO | 94/15901 | 7/1994 |
| WO | 94/15902 | 7/1994 |
| WO | 94/17796 | 8/1994 |
| WO | 95/04036 | 2/1995 |
| WO | 95/07694 | 3/1995 |
| WO | 95/07697 | 3/1995 |
| WO | WO 95/11974 | 5/1995 |
| WO | WO 95/18533 | 7/1995 |
| WO | WO 96/01317 | 1/1996 |
| WO | 96/05165 | 2/1996 |
| WO | 96/13478 | 5/1996 |
| WO | 96/20913 | 7/1996 |
| WO | 96/23884 | 8/1996 |
| WO | WO 96/33724 | 10/1996 |
| WO | 97/10813 | 3/1997 |
| WO | 97/10819 | 3/1997 |
| WO | 97/12853 | 4/1997 |
| WO | 97/25042 | 7/1997 |
| WO | 97/33881 | 9/1997 |
| WO | 98/05331 | 2/1998 |

OTHER PUBLICATIONS

Chen et al. (1993) Biochemical and Biophysical Research Communications 196:671-677.*
Sher et al. (1993) Biochemistry 32:5598-5604.*
Kliewer et al. (1994) Proc Natl. Acad. Sci. USA 91:7355-7359.*
Stratagene (1994) pp. 150-155.*
Wallace et al. (1987) Methods in Enzymology 152:432-442.*
Alihaud, et al., "Cellular and Molecular Aspects of Adipose Tissue Development," *Ann. Rev. Nutr.*, 12:207-233 (1992).
Aperlo, C., et al., "cDNA Cloning and Characterization of the Transcriptional Activities of the Hamster Peroxiosme Proliferator-Activated Receptor HaPPARgamma," Gene., 162:297-302 (1995).
Auwerx, et al., "Transcriptional Activation of the Lipoprotein Lipase and Apolipoprotein E Genes Accompanies Differentiation in Some Human Macrophage-like Cell Lines," *Biochem.*, 27:2651-2655 (1988).
Beers, et al., "The Merk manual of Diagnosis and Therapy." Seventh Edition, 1999. Merck Research Laboratories, Whitehouse Station, NJ., 58-62.
Chawla, "Induction of Rev-ErbAα, an Orphan Receptor Encoded on the Opposite Strand of the α-Thyroid Hormone receptor Gene, during Adipocyte Differentiation," J. Biol. Chem., 268(22):16265-69 (1993).
Chiffelle and Putt, :Histochemical Procedures Sudan Colorants in Propylene Glycol, in *Selected Histochemical and Hisopatholigical Methods*, Charles C. Thomas, Publisher, Springfield, Ill, pp. 329-333 (1996).
Davidson, et al., "A Model System for *in vivo* Gene Transfer Into the Central Nervous System Using an Adenoviral Vector," *Nature Genetics*, 3:219-223 (1993).
Forman, et al., "15-Deoxy-$\Delta^{12,14}$- Prostaglandin $J_2$ is a Ligand for the Adipocyte Determination Factor PPARγ," Cell, 83:803-812 (1995).
Green, S., "PPAR: A Mediator of Peroxisome Proliferator Action," *Mutation Research*, 333(1,2):101-109 (1995).
Greene, et al., "Isolation of the Human Peroxisome Proliferator Activated Receptor Gamma cDNA: Expression in Hematopoietic Cells and Chromosomal Mapping," *Gene Expression*, 4:281-299, (1995).
Kiyoto, "Toward The Treatment of Obesity: Role of PPARγ in Adipogenisis," *Sch. Pharm. Sci.*, Toho Univ., Funabashi, 274 Japan Tanpakushitsu Kakusan Koso 40(13):1936-41 (1995) (Japanese article with English Abstract).

Kliewer, et al., "Convergence Of 9-*Cis* Retinoic Acid And Peroxisome Proliferator Signaling Pathways Through Heterodimer Formation Of Their Receptors," *Nature*, 358:771-774 (1992).
Le Gal La Salle, et al., "An Adenovirus Vector for Gene Transfer into Neurons and Gila in the Brain," *Science*, 259:988-990 (1993).
Lehmann, et al., "An Antidiabetic Thiazolidinedione Is a High Affinity Ligand for Peroxisome Proliferator-activated Receptor γ(PPARγ)*," J. Biol. Chem., 270(22):12953-12956 (1995).
Leibel, et al., Chenges in Energy Expenditure Resulting from Altered Body Weight, *The New Eng., J. of Med.*, 332(10):621-628 (1995).
MacDougald, O.A., et al., "Transcriptional Regulation of Gene Expression During Adipocyte Differentiation,"*Ann. Rev. Biochem.*, 64:345-373 (1995).
Quantin, et al., "Adenovirus as an Expression Vector in Muscle Cells *in vivo*," *Pro. Natl. Acad. Sci. USA*, 89:2581-2584 (1992).
Salazar-Olivo, "Inhibition of 3T3 Adipogenisis by Retinoic Acid is not Mediated by Cytoplasmic Retinoic Acid-Binding Protein," *Biochem. and Biophysical Res. Comm.*, 204(1):257-263 (1994).
Stratford-Perricaudet, et al., "Widespread Long-term Gene Transfer to Mouse Skeletal Muscles and Heart," *J. Clin. Invest*, 90:626-630 (1992).
Thompson, *Selected Histochemical and Histopathological Methods*, Charles C. Thomas, Springfield, Illinois, pp. 329-333 (1996).
Willson, et al., "The Structure-Activity Relationship between Peroxisome Proliferator-Activated Reception Agonism and the Anithyperglycemic Activity of Thiazolidinediones," *J. Med. Chem.*, 39(3):665-668 (1996).
Wu, et al., "Receptor-Mediated Gene Delivery in vivo," *J. Biol. Chem.*, 266(22):14338-14342 (1991).
Zhu, Y,. et al., "Mouse PPAR-gamma gene: Genomic Organization and Promoter Analysis," *Eighty-sixth Annual Meeting of the American Association of Cancer Research*, Toronto, Ontario, CA, Mar. 18-22, 1995. Proceedings of the American Association of Cancer Research Annual Meeting 36.
Barnett et al., "Effect of clofibrate on glucose tolerance in maturity onset diabetes," British Journal of Clinical Pharmacology 4:455-458 (1977).
Derwent Abstract for JP 05 194 209A, published Aug. 3, 1993, entitled "Vascular endothelial cell function improvers—contains fenofibrate e.g. isopropyl 2-(p-(p-cholor:benzoyl)phenoxy)-2-methyl propionate".
Fajas et al., "The Organization, Promoter Analysis, and Expression of the Human PPAR Gene," J. Biol. Chem. 272(30): 18779-18789 (1997).
Gearing et al., "Structure of the Mouse Peroxisome Proliferator Activated Receptor alpha Gene," Biochemical and Biophysical Research Communications 199(1): 255-263 (1994).
Karam, J., "Type II Diabetes and Syndrome X," Endocrinology and Metabolism Clinics of North America 21(2): 329-350 (1992).
Kawamatsu et al., "Studies on Antihyperlipidemic Agents," Arzneim-Forsch 30: 454-459 (1980).
Lenhard et al., "Analysis of Thiazolidinedione, Biguanide and Retinoid Effects on Adipogenesis and the Nuclear Receptors PPARγ and RXR," Diabetologia, Supplement 39(5): A234 (1996).
Tontonoz et al., "Stimulation of adipogenesis in fibroblasts by PPARgamma2, a lipid activated transcription factor," Cell 79:1147-1156 (1994).
Zhu et al., "Structural Organization of Mouse Peroxisome Proliferator-Activated Receptor (mPPAR) Gene: Alternative Promoter Use and Different Splicing Yield Two mPPAR Isoforms," Proc. Natl. Acad. Sci. USA 92: 7921-7925 (1995).
Greene et al, "Isolation of the human peroxisome proliferator activated receptor gamma cDNA: expression in hematopoietic cells and chromosomal mapping," Gene Expression 4:281-299 (1995).
Mukherjee et al, "Identification, characterization, and tissue distribution of human peroxisome proliferator-activated receptor (PPAR) isoforms PPARgamma2 verus PPARgamma1 and activation with retinoid X receptor agonists and antagonists.," J. Biol. Chem. 272:8071-8076 (1997).
Berger et al., "Interaction of Glucocorticoid Analogues with the Human Glucocorticoid Receptor," J. Steroid. Biochem. Molec. Biol. 41: 733-738 (1992).

Boehm et al, "Synthesis and structure-activity relationships of novel retinoid X receptor-selective retinoids," J. of Medicinal Chemistry 37(18):2930-41 (1994).

Broach, J.R., "The Yeast of Plasmid 2µ Circle," In: The Molecular Biology of the Yeast Saccharomyces: Life Cycle and Inheritance, Cold Spring Harbor Laboratory, Cold Spring Harbor, N.Y., pp. 445-470 (1981).

Carter S.K. et al.(Eds.) Chemotherapy of Cancer, 2nd edition, New York: John Wiley & Sons, Appendix C, pp. 364-365 (1981).

Chater et al., "Streptomyces ØC31-Like Phages: Cloning Vectors, Genome Changes and Host Range," In: Sixth International Symposium on Actinomycetes Biology, Debrecen, Hungary, Aug. 26-30, 1985, pp. 45-54 (1986).

Chemical Abstracts Accession No. 123:281583 for Motojima, K, "Toward the treatment of obesity. Role of PPAR Gamma in Adipogensis," Tanpakushitsu Kakusan Koso 40(13):1936-1941 (1995).

Cristiano et al., "Hepatic gene therapy: Adenovirus enhancement of receptor-mediated gene delivery and expression in primary hepatocytes," Proc. Natl. Acad. Sci. USA 90: 2122-2126 (1993).

Crombie et al., "Creatine kinase activity as an indicator of unopposed estrogen action in the mouse uterus associated with antiprogesterone treatment." J. Steroid Biochem Mol Biol. 49(2-3)123-9 (1994).

Dreborg et al., "The chemistry and standardization of allergens," Chapter 10 in the Handbook of Experimental Immunology, 4th Ed., D.M. Weir et al. (Ed.), Oxford ;Boston : Blackwell Scientific Publications, pp. 10.1-10.27(1986).

Freytag et al., "Ectopic expression of the CCAAT/enhancer-binding protein α promotes the adipogenic progamin a variety of mouse fibroblastic cells," Genes Dev. 8:1654-1663 (1994).

Giguere et al., "Functional Domains of the Human Glucocorticoid Receptor," Cell 46:645-652 (1986).

Giguere et al., "Identification of a receptor for the morphogen retinoic acid," Nature 330(2):624-629 (1987).

Grundy et al., "Metabolic and Health Complications of Obesity," Disease-a-Month 36(12):645-696 (1990).

Gryczan, T.J., "Molecular Cloning in Bacillus subtilis," In: The Molecular Biology of the Bacilli, New York: Academic Press, Inc., pp. 307-329 (1982).

Ibrahimi et al., "Evidence for a Common Mechanism of Action for Fatty Acids and Thiazolidinedione Antidiabetic Agents on Gene Expression in Preadipose Cells," Molecular Pharmacology 46:1070-1076 (1994).

Jow, L. and R. Mukherjee, "The human peroxisome proliferator-activated receptor (PPAR) subtype NUC1represses the activation of hPPARα and thyroid hormone receptors,".J Biol Chem. 270(8):3836-40 (1995).

Mangelsdorf et al., "A Direct Repeat in the Cellular Retinol-Binding Protein Type II Gene Confers Differential Regulation by RXR and RAR," Cell 66:555-561 (1991).

Mangelsdorf et al., "Nuclear receptor that identifies a novel retinoic acid response pathway," Nature 345:224-229 (1990).

Maniatis, T., "Recombinant DNA Procedures in the Study of Eukaryotic Genes," In: Cell Biology: A Comprehensive Treatise, vol. 3, Gene Sequence Expression, New York: Academic Press, pp. 563-608 (1980).

Miller et al., "An Insect Baculovirus Host-Vector System for High-Level Expression of Foreign Genes," In: Genetic Engineering: Principles and Methods, Setlow, J. K. et al. (Eds.), New York: Plenum Press , vol. 8, pp. 277-297 (1986).

Motojima, K, "[Toward the treatment of obesity. Role of PPAR Gamma in Adipogenesis]," Tanpakushitsu Kakusan Koso 40(13):1936-1941 (1995) [In Japanese].

Mukherjee, R., "Selective binding of the estrogen receptor to one strand of the estrogen responsive element," Nucleic Acids Res. 21(11):2655-2661 (1993).

Mukherjee et al., "Human and rat peroxisome proliferator activated receptors (PPARs) demonstrate similar tissue distribution but different responsiveness to PPAR activators," J. Steroid Biochem. Mol. Biol. 51(3-4):157-66 (1994).

Nestel, P.J., "Effects of N-3 fatty acids on lipid metabolism," Ann. Rev. Nutr. 10:149-167 (1990).

Ptashne, M., "How eukaryotic transcriptional activators work," Nature 335:683-689 (1988).

Rigas et al., "Lipoprotein alterations in patients treated with novel retinoids," Proceedings of the American Association for Cancer Research, 86th Annual Meeting, Toronto, Ontario, Canada, Mar. 18-22, 1995, vol. 36, p. 506.

Römpp Chemie Lexikon, 9th Extended and Revised Edition, S., Falbe, J. et al. (Eds.) Georg Thieme Verlag Stuggart: New York, pp. 3855-3856 (1992) [Pages in German].

Safonova et al., "Fatty Acids and Retinoids Act Synergistically on Adipose Cell Differentiation," Biochem Biophys Res Commun. 204(2):498-504 (1994).

St. Groth, S.F. and D. Scheideggar, "Production of Monoclonal Antibodies: Strategy and Tactics," Journal of Immunological Methods 35:1-21(1980).

Ullmann's Encyclopedia of Industrial Chemistry, 5th Ed. vol. A8: Coronary Therapeutics to Display Technology, Gerhartz, W. et al. (Eds.) VCH: Weinheim, Federal Republic of Germany), pp. 308-314 (1987).

Umesono et al., "Retinoic acid and thyroid hormone induce gene expression through a common responsive element," Nature 336:262-265 (1988).

Wu, G.Y. and C.H. Wu, "Receptor-mediated in Vitro Gene Transformation by a Soluble DNA Carrier-System," J. Biol. Chem. 262: 4429-4432 (1987).

Zhang et al., "Positional cloning of the mouse obese gene and its human homologue," Nature 372(6505):425-432 (1994).

Zhang et al., "Characterization of Protein-DNA Interactions with the Peroxisome Proliferator-responsive Element of the Rat Hydratase-Dehydrogenase Gene," Journal of Biological Chemistry 268:12939-12945 (1993).

* cited by examiner

SEQUENCE LISTING

<160> NUMBER OF SEQ ID NOS: 7

<210> SEQ ID NO 1
<211> LENGTH: 1936
<212> TYPE: DNA
<213> ORGANISM: Homo sapiens

<400> SEQUENCE: 1

```
gaattccgga ccctcaacac cactccctct tagccaatat tgtgcctatt gccatactag      60
tctttgcgcc tgcgaagcag cggtggccta gccctactag tctcaatctc caacatatat     120
cggcctagac tacgtacata acctaaacct actccaatgc taaaactaat cgtccctttt     180
ctcaaacgag agtcagcctt taacgaaatg accatggttg acacagagat gccattctgg     240
cccaccaact ttgggatcag ctccgtggat ctctccgtaa tggaagacca ctcccactcc     300
tttgatatca agcccttcac tactgttgac ttctccagca tttctactcc acattacgaa     360
gacattccat tcacaagaac agatccagtg gttgcagatt acaagtatga cctgaaactt     420
caagagtacc aaagtgcaat caaagtggag cctgcatctc caccttatta ttctgagaag     480
actcagctct acaataagcc tcatgaagag ccttccaact ccctcatggc aattgaatgt     540
cgtgtctgtg gagataaagc ttctggattt cactatggag ttcatgcttg tgaaggatgc     600 aagggttct tccggagaac aatcagattg aagcttatct atgacagatg tgatcttaac     660
tgtcggatcc acaaaaaaag tagaaataaa tgtcagtact gtcggtttca gaaatgcctt     720
gcagtgggga tgtctcataa tgccatcagg tttgggcgga tgccacaggc cgagaaggag     780
aagctgttgg cggagatctc cagtgatatc gaccagctga atccagagtc cgctgacctc     840
cgggccctgg caaaacattt gtatgactca tacataaagt ccttcccgct gaccaaagca     900
aaggcgaggg cgatcttgac aggaaagaca acagacaaat caccattcgt tatctatgac     960
atgaattcct taatgatggg agaagataaa atcaagttca aacacatcac cccctgcag    1020 gagcagagca aagaggtggc catccgcatc tttcagggct gccagtttcg ctccgtggaa    1080
gctgtgcagg agatcacaga gtatgccaaa agcattcctg gttttgtaaa tcttgacttg    1140
aacgaccaag taactctcct caaatatgga gtccacgaga tcatttacac aatgctggcc    1200
tccttgatga ataaagatgg ggttctcata tccgagggcc aaggcttcat gacaagggag    1260
tttctaaaga gcctgcgaaa gccttttggt gactttatgg agcccaagtt tgagtttgct    1320
gtgaagttca atgcactgga attagatgac agcgacttgg caatattat tgctgtcatt    1380 attctcagtg gagaccgccc aggtttgctg aatgtgaagc ccattgaaga cattcaagac    1440
aacctgctac aagccctgga gctccagctg aagctgaacc accctgagtc ctcacagctg    1500
tttgccaagc tgctccagaa aatgacagac ctcagacaga ttgtcacgga acacgtgcag    1560
```

-continued

```
ctactgcagg tgatcaagaa gacggagaca gacatgagtc ttcacccgct cctgcaggag    1620
atctacaagg acttgtacta gcagagagtc ctgagccact gccaacattt cccttcttcc    1680
agttgcacta ttctgagccg gaattctttt gcttttacc ctggaagaaa tactcataaa    1740
agccgaattc cagcacactg gcggccgtta ctagtggatc cgagctcggt accaagcttg    1800
atgcatagct tgagtatcta tagtgtcacc taaatagctt ggcgtaatca tggtcatagc    1860
tgtttcctgt gtgaaattgt tatccgctca caattccaca caacatacga gccggaagca    1920
taagtgtaaa gcctgg                                                     1936
```

<210> SEQ ID NO 2
<211> LENGTH: 494
<212> TYPE: PRT
<213> ORGANISM: Homo sapiens

<400> SEQUENCE: 2

```
Met Leu Lys Leu Ile Val Pro Phe Leu Lys Arg Glu Ser Ala Phe Asn
  1               5                  10                  15

Glu Met Thr Met Val Asp Thr Glu Met Pro Phe Trp Pro Thr Asn Phe
                 20                  25                  30

Gly Ile Ser Ser Val Asp Leu Ser Val Met Glu Asp His Ser His Ser
             35                  40                  45

Phe Asp Ile Lys Pro Phe Thr Thr Val Asp Phe Ser Ser Ile Ser Thr
         50                  55                  60

Pro His Tyr Glu Asp Ile Pro Phe Thr Arg Thr Asp Pro Val Val Ala
 65                  70                  75                  80

Asp Tyr Lys Tyr Asp Leu Lys Leu Gln Glu Tyr Gln Ser Ala Ile Lys
                 85                  90                  95

Val Glu Pro Ala Ser Pro Pro Tyr Tyr Ser Glu Lys Thr Gln Leu Tyr
            100                 105                 110

Asn Lys Pro His Glu Glu Pro Ser Asn Ser Leu Met Ala Ile Glu Cys
        115                 120                 125

Arg Val Cys Gly Asp Lys Ala Ser Gly Phe His Tyr Gly Val His Ala
    130                 135                 140

Cys Glu Gly Cys Lys Gly Phe Phe Arg Arg Thr Ile Arg Leu Lys Leu
145                 150                 155                 160

Ile Tyr Asp Arg Cys Asp Leu Asn Cys Arg Ile His Lys Lys Ser Arg
                165                 170                 175

Asn Lys Cys Gln Tyr Cys Arg Phe Gln Lys Cys Leu Ala Val Gly Met
            180                 185                 190

Ser His Asn Ala Ile Arg Phe Gly Arg Met Pro Gln Ala Glu Lys Glu
        195                 200                 205

Lys Leu Leu Ala Glu Ile Ser Ser Asp Ile Asp Gln Leu Asn Pro Glu
    210                 215                 220

Ser Ala Asp Leu Arg Ala Leu Ala Lys His Leu Tyr Asp Ser Tyr Ile
225                 230                 235                 240

Lys Ser Phe Pro Leu Thr Lys Ala Lys Ala Arg Ala Ile Leu Thr Gly
                245                 250                 255

Lys Thr Thr Asp Lys Ser Pro Phe Val Ile Tyr Asp Met Asn Ser Leu
            260                 265                 270

Met Met Gly Glu Asp Lys Ile Lys Phe Lys His Ile Thr Pro Leu Gln
        275                 280                 285

Glu Gln Ser Lys Glu Val Ala Ile Arg Ile Phe Gln Gly Cys Gln Phe
    290                 295                 300
```

```
Arg Ser Val Glu Ala Val Gln Glu Ile Thr Glu Tyr Ala Lys Ser Ile
305                 310                 315                 320

Pro Gly Phe Val Asn Leu Asp Leu Asn Asp Gln Val Thr Leu Leu Lys
                325                 330                 335

Tyr Gly Val His Glu Ile Ile Tyr Thr Met Leu Ala Ser Leu Met Asn
                340                 345                 350

Lys Asp Gly Val Leu Ile Ser Glu Gly Gln Gly Phe Met Thr Arg Glu
                355                 360                 365

Phe Leu Lys Ser Leu Arg Lys Pro Phe Gly Asp Phe Met Glu Pro Lys
370                 375                 380

Phe Glu Phe Ala Val Lys Phe Asn Ala Leu Glu Leu Asp Asp Ser Asp
385                 390                 395                 400

Leu Ala Ile Phe Ile Ala Val Ile Ile Leu Ser Gly Asp Arg Pro Gly
                405                 410                 415

Leu Leu Asn Val Lys Pro Ile Glu Asp Ile Gln Asp Asn Leu Leu Gln
                420                 425                 430

Ala Leu Glu Leu Gln Leu Lys Leu Asn His Pro Glu Ser Ser Gln Leu
                435                 440                 445

Phe Ala Lys Leu Leu Gln Lys Met Thr Asp Leu Arg Gln Ile Val Thr
450                 455                 460

Glu His Val Gln Leu Leu Gln Val Ile Lys Lys Thr Glu Thr Asp Met
465                 470                 475                 480

Ser Leu His Pro Leu Leu Gln Glu Ile Tyr Lys Asp Leu Tyr
                485                 490

<210> SEQ ID NO 3
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ctagcgatat catgaccttt gtcctaggcc tc                                    32

<210> SEQ ID NO 4
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4 gatcccttttg acctattgaa ctattaccta catta                                35

<210> SEQ ID NO 5
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gatccccact gaacccttga cccctgccct gcagca                                36
```

-continued

```
<210> SEQ ID NO 6
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ctaggaggcc taggacaaag gtcatgatat cg                                    32

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
cccgaacgtg acctttgtcc tggtcc                                           26
```

HUMAN PEROXISOME PROLIFERATOR ACTIVATED RECEPTOR γ

CROSS REFERENCE TO RELATED APPLICATIONS

This application is a continuation-in-part of U.S. application Ser. No. 08/380,051, entitled "Human Peroxisome Proliferator Activated Receptor γ", filed Jan. 30, 1995, by Mukherjee, now abandoned, the disclosure of which is incorporated by reference herein.

FIELD OF THE INVENTION

This invention relates to screening for agents active on peroxisome proliferator activated receptor (PPAR). This invention also relates to the cloning and uses of a human peroxisome proliferator activated receptor subtype.

BACKGROUND OF THE INVENTION

Peroxisomes are subcellular organelles found in animals and plants. Peroxisomes contain enzymes for cholesterol and lipid metabolism and respiration.

A variety of chemical agents called peroxisome proliferators induce the proliferation of peroxisomes and increase the capacity of peroxisomes to metabolize fatty acids via increased expression of the enzymes required for the β-oxidation cycle. Peroxisome proliferators include unsaturated fatty acids, hypolipidemic drugs (Reddy, J. K., and Azarnoff, D. L., *Nature* 283:397–398, 1980), herbicides, leukotriene antagonists, and plasticizers (for a review, see Green, S., *Biochem. Pharmacol.* 43:393–400, 1992). Hypolipidemic drugs such as clofibrates have been found to lower triglycerides and cholesterol levels in plasma and to be beneficial in the prevention of ischemic heart disease in individuals with elevated levels of cholesterol (Havel, R. J. and Kane, J. P., *Ann. Rev. Pharmac.* 13:287–308, 1973). However, fibrate hypolipidemic drugs are also rodent hepatocarcinogens (Reddy, J. K., et al., *Br. J. Cancer* 40:476–482, 1979; Reddy, J. K., et al., *Nature* 283:397–398, 1980).

There are two hypotheses for peroxisome proliferation. The "lipid overload hypothesis" suggests that an increase in the intracellular concentration of fatty acids is the main stimulus for peroxisome proliferation (Nestel, P. J., *Ann. Rev. Nutr.* 10:149–167, 1990, and Phillipson, B. E., et al., *N. Engld. J. Med.* 312:1210–1216, 1985).

Another hypothesis postulates a receptor mediated mechanism. Peroxisome proliferator activated receptors (PPARs) have been isolated and cloned from various species (Isseman, I., and Green, S., *Nature* 347:645–650, 1990; Dreyer, C., et al., *Cell* 68:879–887, 1992; Gottlicher, M., et al., *Proc. Natl. Acad. Sci. USA*. 89:4653–4657, 1992; Sher, T., et al., *Biochemistry* 32:5598–5604, 1993; and Schmidt, A., et al., *Mol. Endocrinol.* 6:1634–16414–8, 1992). The ligand for PPARs is still unidentified.

PPARs belong to the nuclear hormone receptor superfamily. Some members of the superfamily are receptors for the classical steroid hormones; and others bind thyroid hormones, vitamin $D_3$ and retinoic acid. However, the putative ligands for many remain to be identified, and such receptors have been termed orphan receptors. Nuclear hormone receptors are intracellular proteins that are ligand-dependent transcription modulators. They usually have a ligand binding domain that binds the cognate ligand with high affinity and specificity. They usually also have a DNA binding domain that recognizes short DNA motifs generally termed Hormone Response Elements (HREs).

Issemann and Green, *Nature* 347:645–650, 1990, cloned a mouse peroxisome proliferator activated receptor (mPPARα) gene from a mouse liver complementary DNA (cDNA) library. Chimeric receptors constructed using the DNA binding domain of either the estrogen or glucocorticoid receptor and the putative ligand binding domain of mPPAR are able to activate, respectively, an estrogen- or glucocorticoid-responsive gene in the presence of peroxisome proliferators. mPPARα protein binds to a specific peroxisome proliferator response element (PPRE) located 570 bp upstream of the rat acyl-CoA oxidase gene, which is a key marker of peroxisome proliferator action (Tugwood, J. D., et al. *EMBO J.* 11:433–439, 1992).

Göttlicher et al., *Proc. Nat. Acad. Sci. USA* 89:4653–4657, 1992, cloned a rat peroxisome proliferator activated receptor (rPPAR) gene from a rat liver cDNA library. PPARs from mouse and rat share 97% homology in amino acid sequence and a particularly well-conserved putative ligand-binding domain. Three members of the *Xenopus* nuclear hormone receptor superfamily (i.e., XPPARα, XPPARβ and XPPARγ) have also been found to be structurally and functionally related to the mPPARα (Dreyer et al., *Cell* 68:879–887, 1992). Schmidt et al., *Molecular Endocrinology* 6:1634–1641, 1992, cloned a steroid hormone receptor gene, hNUC1 (also known as hPPARβ), from a human osteosarcoma cell cDNA library. The homology between amino acid sequence of hNUC1 and that of mPPARα is 62%.

Chen et al., *Biochem. Biophy. Res. Com.* 196:671–677, 1993, cloned two mouse PPAR genes, mNUC1 and mPPARγ, from a neonatal mouse brain cDNA library and an adult mouse heart cDNA library, respectively.

Zhu et al., *J. Biological Chemistry* 268:26817–26820, 1993, cloned a mPPARγ gene from mouse liver cDNA library encoding a 475-amino acid protein with 75% amino acid similarity to XPPARγ, and 55% identity with mPPARα.

Tontonoz et al., *Genes &Development* 8:1224–34, 1994, not admitted to be prior art, cloned a mPPARγ2 gene from a mouse adipocyte cDNA library. mPPARγ2 protein is an adipocyte-specific transcription factor. It is highly expressed in white adipose tissue and is dramatically induced during differentiation of preadipocytes into adipocytes.

Kliewer et al., *Proc. Natl. Acad. Sci. USA* 91:7355–59, 1994, not admitted to be prior art, cloned mPPARγ and mPPARδ genes from a mouse liver cDNA library.

Two subtypes of PPAR receptors, α and β, have been characterized from humans (see, Sher et al., *Biochemistry* 32:5598–5604, 1993, and Schmidt et al., *Molecular Endocrinology* 6:1634–1641, 1992).

SUMMARY OF THE INVENTION

In related U.S. application Ser. No. 08/270,635, entitled "Screening for NUC Inhibitors," filed Jul. 1, 1994, by Mukherjee, and U.S. application Ser. No. 08/143,215, entitled "Human Peroxisome Proliferator Activated Receptor," filed Oct. 25, 1993, by Mukherjee, which is a continuation-in-part of application Ser. No. 08/141,500, entitled "Human Peroxisome Proliferator Activated Receptor," filed Oct. 22, 1993, by Mukherjee, applicant has isolated two human PPAR subtypes, i.e., PPARα and hNUC1B. However, the lack of a human PPARγ cDNA clone has hampered research such as an examination of the expression patterns of the PPAR family of receptors in human tissues and cell lines. To alleviate this problem we cloned and characterized a human PPARγ subtype cDNA.

The present invention relates to hPPARγ polypeptides, nucleic acids encoding such polypeptides, cells, tissues and animals containing such polypeptides and nucleic acids, antibodies to such polypeptides, assays utilizing such polypeptides and nucleic acids, and methods relating to all of the foregoing. The hPPARγ polypeptides, nucleic acids, and antibodies are useful for establishing the tissue specific expression pattern of hPPARγ gene. For example, a Northern blot can be used to reveal tissue specific expression of the gene. They are also useful for screening for agonists and antagonists of hPPARγ peptides for improved pharmacological profiles for the treatment of diseases with higher potency, efficacy, and fewer side effects.

The present invention is based upon the identification and isolation of a novel human peroxisome proliferator activated receptor subtype termed hPPARγ.

Applicant has determined that hPPARγ polypeptide represses hPPARα (hPPARα, referred to as hPPAR1 in U.S. application Ser. No. 08/143,215, is a subtype of PPAR) activity, and that relief from such repression is therapeutically useful. hPPARγ polypeptides bind to peroxisome proliferator response elements (PPREs) as a complex with RXR polypeptides (e.g., RXRα, β or γ). hPPARγ polypeptides are not significantly activated by compounds that activate mPPARα polypeptides. hPPARγ polypeptide repress hPPARα polypeptides' transcription activation activity by sequestering RXR polypeptides.

The present invention features methods for identifying agonists and antagonists of hPPARγ polypeptides. The present invention also features methods for identifying therapeutic agents that alleviate the repressive effects of hPPARγ polypeptides on PPARα polypeptides' transcription activation activity. These methods make it possible to screen large collections of natural, semisynthetic, or synthetic compounds for therapeutically useful profiles. hPPARγ agonists, antagonists, and agents that alleviate the repressive effects of hPPARγ polypeptides on PPARα polypeptides may be used to treat diseases and pathological conditions affected by the level of hPPARγ polypeptide activity, such as, but not limited to, obesity, diabetes, hyperlipidemia, hypercholesteremia and hyper-lipoproteinemia.

This invention is also directed to compounds, compositions, and methods for treating a patient exhibiting a pathological condition affected by the level of hPPARγ polypeptide activity. More particularly, the invention relates to hPPARγ agonists, antagonists, and compounds and pharmaceutical compositions that relieve the repression of PPARα activity by a hPPARγ polypeptide.

Thus, in a first aspect the invention features an isolated, purified, enriched or recombinant nucleic acid encoding a hPPARγ polypeptide.

By "isolated" in reference to nucleic acid is meant a polymer of 2 (preferably 21, more preferably 39, most preferably 75) or more nucleotides conjugated to each other, including DNA or RNA that is isolated from a natural source or that is synthesized. The isolated nucleic acid of the present invention is unique in the sense that it is not found in a pure or separated state in nature. Use of the term "isolated" indicates that a naturally occurring sequence has been removed from its normal cellular environment. Thus, the sequence may be in a cell-free solution or placed in a different cellular environment. The term does not imply that the sequence is the only nucleotide chain present, but does indicate that it is the predominate sequence present (at least 10–20% more than any other nucleotide sequence) and is essentially free (about 90–95% pure at least) of non-nucleotide material naturally associated with it. Therefore, the term does not encompass an isolated chromosome encoding a hPPARγ polypeptide.

By "purified" in reference to nucleic acid does not require absolute purity (such as a homogeneous preparation); instead, it represents an indication that the sequence is relatively purer than in the natural environment (compared to the natural level this level should be at least 2–5 fold greater, e.g., in terms of mg/ml). Individual clones isolated from a cDNA library may be purified to electrophoretic homogeneity. The claimed DNA molecules obtained from these clones could be obtained directly from total DNA or from total RNA. The cDNA clones are not naturally occurring, but rather are preferably obtained via manipulation of a partially purified naturally occurring substance (messenger RNA). The construction of a cDNA library from mRNA involves the creation of a synthetic substance (cDNA) and pure individual cDNA clones can be isolated from the synthetic library by clonal selection of the cells carrying the cDNA library. Thus, the process which includes the construction of a cDNA library from mRNA and isolation of distinct cDNA clones yields an approximately $10^6$-fold purification of the native message. Thus, purification of at least one order of magnitude, preferably two or three orders, and more preferably four or five orders of magnitude is expressly contemplated.

By "enriched" in reference to nucleic acid is meant that the specific DNA or RNA sequence constitutes a significantly higher fraction (2–5 fold) of the total DNA or RNA present in the cells or solution of interest than in normal or diseased cells or in the cells from which the sequence was taken. This could be caused by a person by preferential reduction in the amount of other DNA or RNA present, or by a preferential increase in the amount of the specific DNA or RNA sequence, or by a combination of the two. However, it should be noted that enriched does not imply that there are no other DNA or RNA sequences present, just that the relative amount of the sequence of interest has been significantly increased in a useful manner and preferably separate from a sequence library. The term "significantly" here is used to indicate that the level of increase is useful to the person making such an increase, and generally means an increase relative to other nucleic acids of about at least 2 fold, more preferably at least 5 to 10 fold or even more. The term also does not imply that there is no DNA or RNA from other sources. The DNA from other sources may, for example, comprise DNA from a yeast or bacterial genome, or a cloning vector such as pUC19. This term distinguishes from naturally occurring events, such as viral infection, or tumor type growths, in which the level of one mRNA may be naturally increased relative to other species of mRNA. That is, the term is meant to cover only those situations in which a person has intervened to elevate the proportion of the desired nucleic acid.

By "recombinant" in reference to a nucleic acid is meant the nucleic acid is produced by recombinant DNA techniques such that it is distinct from a naturally occurring nucleic acid.

By "a hPPARγ polypeptide" is meant two or more contiguous amino acids set forth in the full length amino acid sequence of SEQ ID NO:2, wherein said contiguous amino acids have a sequence different from those of mouse or *Xenopus* PPARγ polypeptides. The hPPARγ polypeptide can be encoded by a full-length nucleic acid sequence or any portion of the full-length nucleic acid sequence, so long as a functional activity of the polypeptide is retained. For example, the DNA-binding domain of a hPPARγ polypeptide may be replaced with the DNA-binding domain of another nuclear hormone receptor.

In preferred embodiments the nucleic acid comprises, consists essentially of, or consists of a nucleic acid sequence set forth in the full length nucleic acid sequence SEQ ID NO:1 or at least 27, 30, 45, 60 or 90 contiguous nucleotides thereof and the hPPARγ polypeptide comprises, consists essentially of, or consists of at least 9, 10, 15, 20, or 30 contiguous amino acids of a hPPARγ polypeptide.

By "comprising" is meant including, but not limited to, whatever follows the word "comprising". Thus, use of the term "comprising" indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

In other preferred embodiments, the nucleic acid comprises no less than 60 contiguous nucleotides from sequence numbers 157 to 1641 or 214 to 1641 of SEQ. ID. NO.1.

Compositions and probes of the present invention may contain human nucleic acid encoding a hPPARγ polypeptide but are substantially free of nucleic acid not encoding a human hPPARγ polypeptide. The human nucleic acid encoding a hPPARγ polypeptide is at least 18 contiguous bases of the nucleotide sequence set forth in SEQ. ID NO. 1 and will selectively hybridize to human genomic DNA encoding a hPPARγ polypeptide, or is complementary to such a sequence. The nucleic acid may be isolated from a natural source by cDNA cloning or subtractive hybridization; the natural source may be blood, semen, and tissue of humans; and the nucleic acid may be synthesized by the triester method or by using an automated DNA synthesizer. In yet other preferred embodiments the nucleic acid is a unique region, for example those useful for the design of hybridization probes to facilitate identification and cloning of additional polypeptides, the design of PCR probes to facilitate cloning of additional polypeptides, and obtaining antibodies to polypeptide regions.

By "unique nucleic acid region" is meant a sequence present in a full length nucleic acid coding for a hPPARγ polypeptide that is not present in a sequence coding for any other naturally occurring polypeptide. Such regions preferably comprise 12 or 20 contiguous nucleotides present in the full length nucleic acid encoding a hPPARγ polypeptide.

The invention also features a nucleic acid probe for the detection of a hPPARγ polypeptide or nucleic acid encoding a hPPARγ polypeptide in a sample. The nucleic acid probe contains nucleic acid that will hybridize to a sequence set forth in SEQ ID NO:1, but not to a mouse PPARγ nucleic acid sequence under high stringency hybridization conditions. In preferred embodiments the nucleic acid probe hybridizes to nucleic acid encoding at least 12, 27, 30, 35, 40 or 50 contiguous amino acids of the full-length sequence set forth in SEQ ID NO:2.

By "high stringency hybridization conditions" is meant those hybridizing conditions that (1) employ low ionic strength and high temperature for washing, for example, 0.015 M NaCl/0.0015 M sodium citrate/0.1% SDS at 50° C.; (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C.; or (3) employ 50% formamide, 5×SSC (0.75 M NaCl, 0.075 M Sodium pyrophosphate, 5× Denhardt's solution, sonicated salmon sperm DNA (50 g/ml), 0.1% SDS, and 10% dextran sulfate at 42° C., with washes at 42° C. in 0.2×SSC and 0.1% SDS. Under stringent hybridization conditions only highly complementary nucleic acid sequences hybridize. Preferably, such conditions prevent hybridization of nucleic acids having 1 or 2 mismatches out of 20 contiguous nucleotides.

Methods for using the probes include detecting the presence or amount hPPARγ RNA in a sample by contacting the sample with a nucleic acid probe under conditions such that hybridization occurs and detecting the presence or amount of the probe bound to hPPARγ RNA. The nucleic acid duplex formed between the probe and a nucleic acid sequence coding for a hPPARγ polypeptide may be used in the identification of the sequence of the nucleic acid detected (for example see, Nelson et al., in *Nonisotopic DNA Probe Techniques*, p. 275 Academic Press, San Diego (Kricka, ed., 1992) hereby incorporated by reference herein in its entirety, including any drawings). Kits for performing such methods may be constructed to include a container means having disposed therein a nucleic acid probe.

The invention features recombinant nucleic acid comprising a contiguous nucleic acid sequence encoding a hPPARγ polypeptide, preferably in a cell or an organism. The recombinant nucleic acid may contain a sequence set forth in SEQ ID NO:1 and a vector or a promoter effective to initiate transcription in a host cell. The recombinant nucleic acid can alternatively contain a transcriptional initiation region functional in a cell, a sequence complimentary to an RNA sequence encoding a hPPARγ polypeptide and a transcriptional termination region functional in a cell.

In preferred embodiments, the recombinant nucleic acid comprises no less than 60 contiguous nucleotides from sequence numbers 157 to 1641 or 214 to 1641 of SEQ. ID. NO.1.

In another aspect the invention features an isolated, enriched, purified or recombinant hPPARγ polypeptide.

By "isolated" in reference to a polypeptide is meant a polymer of 2 (preferably 7, more preferably 13, most preferably 25) or more amino acids conjugated to each other, including polypeptides that are isolated from a natural source or that are synthesized. The isolated polypeptides of the present invention are unique in the sense that they are not found in a pure or separated state in nature. Use of the term "isolated" indicates that a naturally occurring sequence has been removed from its normal cellular environment. Thus, the sequence may be in a cell-free solution or placed in a different cellular environment. The term does not imply that the sequence is the only amino acid chain present, but that it is the predominate sequence present (at least 10–20% more than any other sequence) and is essentially free (about 90–95% pure at least) of non-amino acid material naturally associated with it.

By "enriched" in reference to a polypeptide is meant that the specific amino acid sequence constitutes a significantly higher fraction (2–5 fold) of the total of amino acids present in the cells or solution of interest than in normal or diseased cells or in the cells from which the sequence was taken. This could be caused by a person by preferential reduction in the amount of other amino acids present, or by a preferential increase in the amount of the specific amino acid sequence of interest, or by a combination of the two. However, it should be noted that enriched does not imply that there are no other amino acid sequences present, just that the relative amount of the sequence of interest has been significantly increased. The term "significantly" here is used to indicate that the level of increase is useful to the person making such an increase, and generally means an increase relative to other amino acids of about at least 2 fold, more preferably at least 5 to 10 fold or even more. The term also does not imply that there is no amino acid from other sources. The amino acid from other sources may, for example, comprise amino acid encoded by a yeast or bacterial genome, or a cloning vector such as pUC19. The term is meant to cover only those situations in which man has intervened to elevate the proportion of the desired amino acid.

By "purified" in reference to a polypeptide does not require absolute purity (such as a homogeneous preparation); instead, it represents an indication that the sequence is relatively purer than in the natural environment (compared to the natural level this level should be at least 2–5 fold greater, e.g., in terms of mg/ml). Purification of at least one order of magnitude, preferably two or three orders, and more preferably four or five orders of magnitude is expressly contemplated. The substance is preferably free of contamination at a functionally significant level, for example 90%, 95%, or 99% pure.

By "recombinant hPPARγ polypeptide" is meant a hPPARγ polypeptide produced by recombinant DNA techniques such that it is distinct from a naturally occurring polypeptide either in its location (e.g., present in a different cell or tissue than found in nature), purity or structure. Generally, such a recombinant polypeptide will be present in a cell in an amount different from that normally observed in nature. This invention features recombinant hPPARγ polypeptides obtainable using techniques known to those skilled in the art, including those described in McDonnell et al., U.S. patent application Ser. No. 08/223,943 filed Apr. 6, 1994, Evans et al., U.S. Pat. No. 5,071,773, and PCT application, PCT/US91/00399 filed Jan. 22, 1991 (International Publication No. WO 91/12258), incorporated by reference herein.

In a preferred embodiment, either vector pBacPAK8 (Clontech) or vector pBacPAK9 (Clontech) is used to express recombinant hPPARγ polypeptide in insect cells. In another preferred embodiment, vector pYES2 (Invitrogen) is used to express recombinant hPPARγ polypeptide in yeast cells. In yet another preferred embodiment, pBKCMV (Stratagene) is used to express recombinant hPPARγ polypeptide in mammalian cells.

In preferred embodiments the hPPARγ polypeptide contains at least 9, 10, 15, 20, or 30 contiguous amino acids of the full-length sequence set forth in SEQ ID NO:2.

In yet another aspect the invention features an isolated, enriched, or purified antibody (e.g., a monoclonal or polyclonal antibody) having specific binding affinity to a hPPARγ polypeptide. The antibody contains a sequence of amino acids that is able to specifically bind to a hPPARγ polypeptide. An anti-peptide antibody may be prepared with techniques known to those skilled in the art, including, but not limited to, those disclosed in Niman, PCT application PCT/US88/03921 (International Publication No. WO 89/04489), incorporated by reference herein.

By "specific binding affinity" is meant that the antibody will bind to a hPPARγ polypeptide at a certain detectable amount but will not bind other polypeptides to the same extent under identical conditions.

Antibodies having specific binding affinity to a hPPARγ polypeptide may be used in methods for detecting the presence and/or amount of a hPPARγ polypeptide in a sample by contacting the sample with the antibody under conditions such that an immunocomplex forms and detecting the presence and/or amount of the antibody conjugated to the hPPARγ polypeptide. Diagnostic kits for performing such methods may be constructed to include a first container means containing the antibody and a second container means having a conjugate of a binding partner of the antibody and a label.

In another aspect the invention features a hybridoma which produces an antibody having specific binding affinity to a hPPARγ polypeptide.

By "hybridoma" is meant an immortalized cell line which is capable of secreting an antibody, for example a hPPARγ antibody.

In preferred embodiments the hPPARγ antibody comprises a sequence of amino acids that is able to specifically bind a hPPARγ polypeptide.

In other aspects, the invention provides transgenic, non-human mammals containing a transgene encoding a hPPARγ polypeptide or a gene effecting the expression of a hPPARγ polypeptide. Such transgenic nonhuman mammals are particularly useful as an in vivo test system for studying the effects of introducing a hPPARγ polypeptide, regulating the expression of a hPPARγ polypeptide (i.e., through the introduction of additional genes, antisense nucleic acids, ribozymes, or hPPARγ agonists or antagonists).

A "transgenic animal" is an animal having cells that contain DNA which has been artificially inserted into a cell, which DNA becomes part of the genome of the animal which develops from that cell. Preferred transgenic animals are primates, mice, rats, cows, pigs, horses, goats, sheep, dogs and cats. The transgenic DNA may encode for a hPPARγ polypeptide. Native expression in an animal may be reduced by providing an amount of anti-sense RNA or DNA effective to reduce expression of the receptor.

In another aspect, the invention describes a recombinant cell or tissue containing a purified nucleic acid coding for a hPPARγ polypeptide. In such cells, the nucleic acid may be under the control of its genomic regulatory elements, or may be under the control of exogenous regulatory elements including an exogenous promoter. By "exogenous" it is meant a promoter that is not normally coupled in vivo transcriptionally to the coding sequence for the hPPARγ polypeptide.

In another aspect, the invention features a method for screening for a therapeutic agent for treatment of a pathological condition affected by a hPPARγ polypeptide by detecting an agonist or antagonist of the hPPARγ polypeptide.

A cell or an in vitro system is transformed with a vector expressing the hPPARγ polypeptide and a reporter gene whose expression is activated by the hPPARγ polypeptide. The cell or in vitro system is brought into contact with a test compound. An increase in the expression of the reporter gene would indicate that the test compound is an agonist of the hPPARγ polypeptide; a decrease in the expression of the reporter gene would indicate that the test compound is an antagonist of the hPPARγ polypeptide.

In a preferred embodiment, the vector contains translation initiation squence operationaly linked to a sequence encoding the hPPARγ polypeptide. The hPPARγ polypeptide begins with the third, second or first methionine in SEQ. ID. NO. 2.

By "reporter gene" is meant a gene encoding a product that is easily detected and assayed by techniques known to those skilled in the art. A reporter gene in this invention is driven by a promoter that is responsive to hPPARγ polypeptides, or PPARα polypeptides, including, but not limited to, the native promoter of a gene such as acylcoenzyme A oxidase, enoyl-CoA hydratase/3-hydrosyacyl-CoA dehydrogenase bifunctional enzyme, 3-ketoacyl thiolase or ApoA1.

In another preferred embodiment, the reporter gene comprises a peroxisome proliferator responsive element (PPRE element) that is responsive to hPPARγ polypeptide activation. The hPPARγ gene and the reporter gene are encoded in vectors and introduced into the cell by co-transfection.

Co-transfection assays may be performed as previously described (Heyman, et al. *Cell* 68:397–406, (1992); Allegretto, et al. *J. Biol. Chem.* 268:26625–26633 (1993); Isseman, I., and Green, S., *Nature* 347:645–650, 1990). In an example, the DNA-binding domain of hPPARγ is replaced with the DNA-binding domain of a well characterized nuclear receptor, including, but not limited to, the glucocorticoid or estrogen receptor, to create a chimeric receptor able to activate a glucocorticoid- or estrogen-responsive reporter gene in the presence of the hPPARγ-specific ligand (Giguere, V. and Evans, RM 1990, "Identification of receptors for retinoids as members of the steroid and thyroid hormone receptor family", In: Packer L (ed) Retinoids. Part A: Molecular and Metabolic Aspects. *Methods in Enzymology*. Academic Press, San Diego, Calif., 189:223–232, incorporated by reference herein). The cell is transformed with the chimeric receptor. The cell is also transformed with a reporter vector which comprises a segment encoding a reporter polypeptide under the control of a promoter and a segment of hormone response element (such as a glucocorticoid- or estrogen-responsive element).

The reporter gene may be expressed at a basal level in the cell. When a suitable agonist is provided to the cell, the hPPARγ polypeptide is transformed and delivered to an appropriate DNA-binding region of the reporter gene to thereby activate the hormone response element and increase the expression of the reporter gene. On the other hand, when a suitable antagonist is provided to the cell, the expression of the reporter gene is decreased to less than the basal level. Activation or inactivation of the reporter gene is detected by standard procedures used for detecting the product of a reporter gene. After introduction of the chimeric receptor and report gene constructs in recipient cells by transient transfection, the cells are challenged with a battery of compounds until an activation or inactivation response is observed.

Because PPARγ has been implicated in adipose cell function and development, hPPARγ agonists and antagonists may be useful for treating obesity, diabetes, anorexia, lipoprotein defects, hyperlipidemia, hypercholesteremia and hyperlipoproteinemia and other related disorders. PPARγ is a key receptor in the differentiation step from preadipocytes to adipocytes. PPARγ is an adipocyte specific-nuclear hormone receptor that has been identified as a key regulator of certain fat cell enhancers (Tontonez et al., *Cell* 79:1147–1156, 1994). Overexpressing PPARγ stimulates adipose differentiation in non-adipogenic cell lines like fibroblasts.

PPARγ antagonists may be used to block or reverse the differentiation step from preadipocytes to adipocytes. RXR agonists or antagonists may also be used to block or reverse this differentiation step since PPARγ binds to DNA as a heterodimer with RXR. Such compounds would be useful in the treatment of obesity, diabetes, anorexia, lipoprotein defects, hyperlipidemia, hypercholesteremia and hyperlipoproteinemia and related disorders.

In another aspect, the present invention features a method for identifying therapeutic agents for treatment of a pathological condition affected by a hPPARγ polypeptide, by screening for therapeutic agents which, when added to a system containing the hPPARγ polypeptide and PPARα protein, relieve the repression of PPARα protein activity by the hPPARγ polypeptide.

In a preferred embodiment, a hPPARγ polypeptide, PPARα protein and reporter gene are provided in a cell or an in vitro system. The reporter gene has a peroxisome proliferator responsive element (PPRE) and can be activated by the PPARα protein. The hPPARγ polypeptide represses the expression of the reporter gene. The reduction or relief of the repression of the PPARα protein by the hPPARγ polypeptide is measured by the expression level of the reporter gene.

In a further preferred embodiment, hPPARγ gene, PPARα gene and a reporter gene are encoded in vectors and introduced into a cell by transfection.

In another further preferred embodiment, a PPAR activator is added to the screening assay.

By "PPAR activator" is meant a chemical agent that is capable of activating the transcription activation activity of PPAR protein, such as, but not limited to, CFA (clofibric acid), ETYA (5,8,11,14-eicosatetraynoic acid) or WY-14, 643 ([4-chloro-6-(2,3-xylidino)-2-pyrimidinylthio]acetic acid).

In yet another preferred embodiment, the reporter gene comprises a PPRE element.

In other preferred embodiments, this method screens for agents that interfere with the formation of a heterodimer between a hPPARγ polypeptide and a RXR polypeptide such as RXRα, RXRβ, or RXRγ, or the binding of a heterodimer between a hPPARγ polypeptide and a RXR polypeptide to a PPRE element.

By boosting PPARα activity, the agents that relieve the repression of PPARα protein activity by hPPARγ may enhance the effects of PPARα agonists and be helpful for treating obesity, diabetes, hyperlipidemia, hypercholesteremia and hyperlipoproteinemia.

In another aspect, this invention features a method for treatment of a pathological condition affected by the level of hPPARγ activity by providing an agonist, an antagonist, or an agent that represses or reduces the repression of PPARα protein activity by hPPARγ polypeptides. The pathological conditions treated by this method include, but are not limited to, obesity, diabetes, anorexia, lipoprotein defects, hyperlipidemia, hypercholesteremia, hyperlipoproteinemia and other metabolic diseases.

The present invention also features novel or unique compounds identified by methods described above that are hPPARγ agonists, hPPARγ antagonists, or capable of repressing or reducing the repression of PPARα protein activity by hPPARγ polypeptides. By "novel or unique" is meant that the compounds are not known per se or are not already known for uses relating to treatment of a pathological condition affected by the level of hPPARγ polypeptides.

Applicant is particularly interested in the identification of agents of low molecular weight (less than 10,000 daltons, preferably less than 5,000, and most preferably less than 1,000) which can be readily formulated as useful therapeutic agents.

Such agents can then be screened to ensure that they are specific to tissues with pathological conditions induced or aggravated by human PPARγ protein with little or no effect on healthy tissues such that the agents can be used in a therapeutic or prophylactic manner. If such agents have some effect on healthy tissues they may still be useful in therapeutic treatment, particularly in those diseases which are life threatening.

By antagonizing hPPARγ, the agents will be helpful to reduce adipocyte differentiation for treating obesity, diabetes and other lipoprotein defects.

The compounds identified by the method of this invention are particularly useful in the treatment of diseases and pathological conditions affected by the level of hPPARγ polypeptides, including, without limitation, obesity, diabetes, anorexia, lipoprotein defects, hyperlipidemia, hypercholesteremia and hyperlipoproteinemia.

The present invention also includes pharmaceutically acceptable compositions prepared for storage and subsequent administration which include a pharmaceutically effective amount of an above-described product in a pharmaceutically acceptable carrier or diluent.

By "therapeutically effective amount" is meant an amount of a pharmaceutical composition having a therapeutically relevant effect. A therapeutically relevant effect relieves to some extent one or more symptoms of the disease or condition in the patient; or returns to normal either partially or completely one or more physiological or biochemical parameters associated with or causative of the disease or condition.

Other features and advantages of the invention will be apparent from the following description of the preferred embodiments thereof, and from the claims.

CV-1 cells were transfected with 0.1 µg pCMVhPPARγ or the empty expression vector pBKCMV (no receptor). LY-171,883, 9-cis-retinoic acid, ETYA and gemfibrozil were added. Fold induction is defined as the ratio of the maximal response observed in the presence of the compound to that in its absence.

Figure 2:
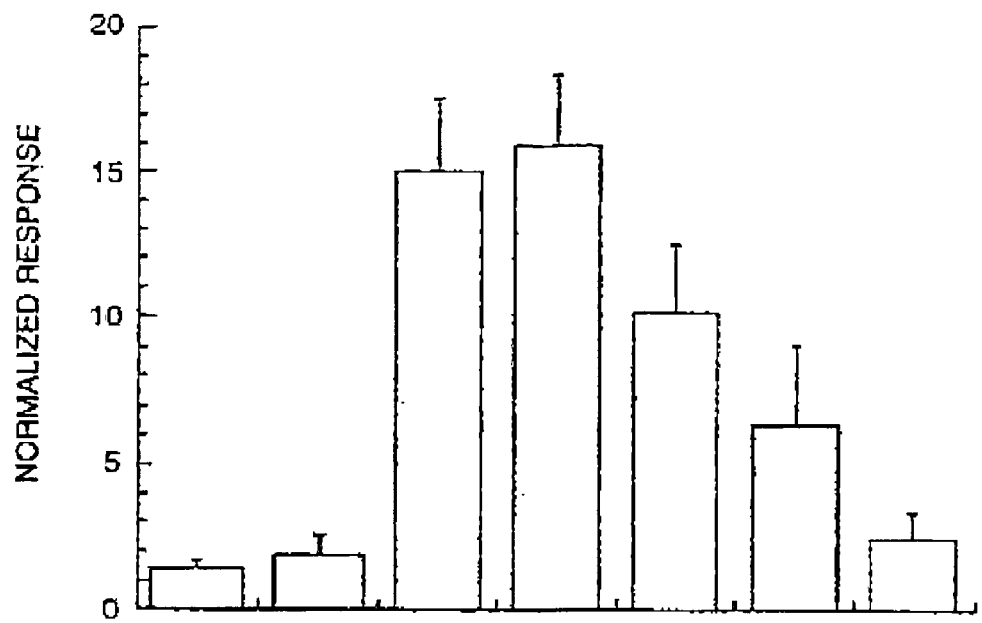

FIG. 2 is a graph showing normalized response of a reporter gene to steady dose of hPPARα coupled with increasing dose of hNUC or hPPARγ.

CV-1 cells were transfected with 0.1 µg of pCMVhPPARα and 0.1 or 0.4 µg of pCMVhNUC1 or pCMVhPPARγ. Gemfibrozil was added to a final concentration of 100 M.

Figure 3A:
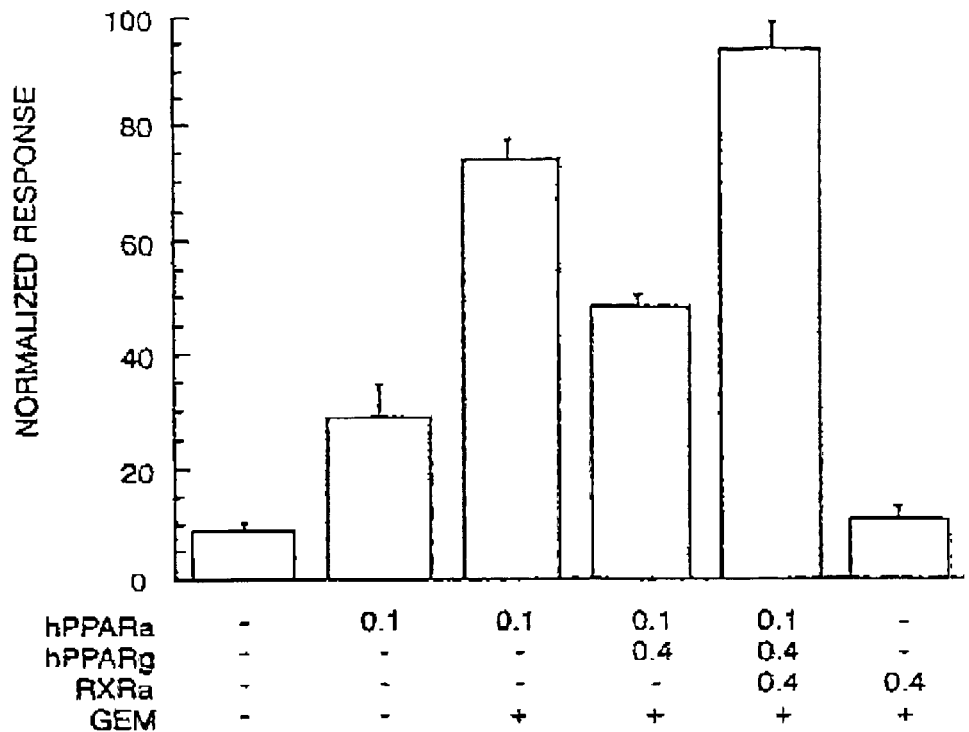
Figure 3B:
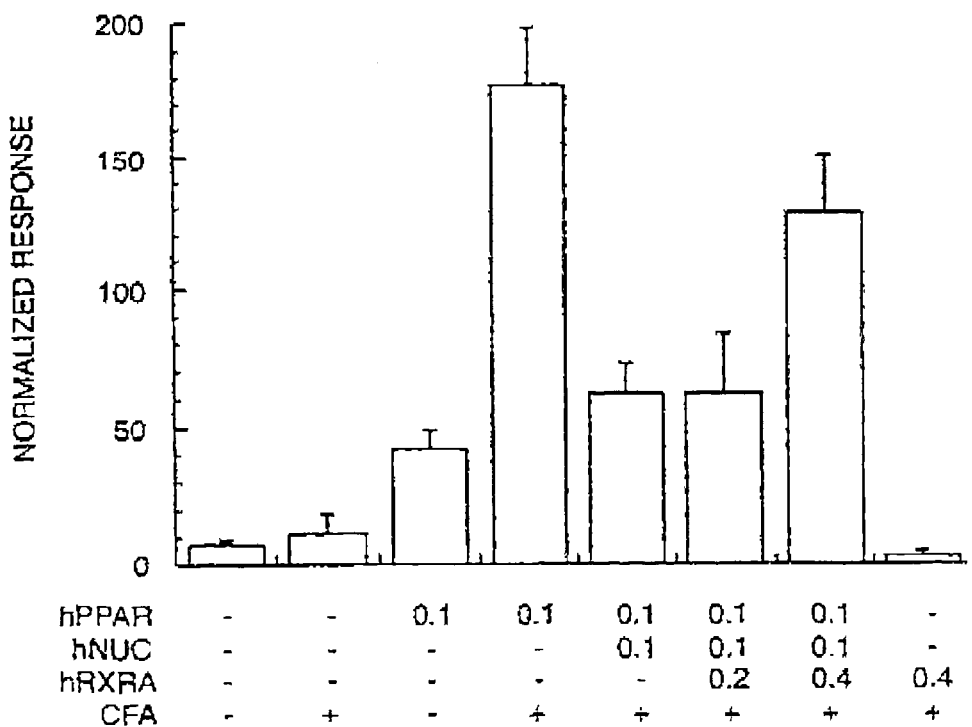

FIG. 3 is a graph showing normalized response of a reporter gene to mixing doses of hPPARα, hPPARγ, hRXRα, and hNUC.

HepG2 cells were transfected with 0.1 µg of pCMVhPPARα and 0.4 µg of hPPAR (A) or 0.1 µg of hNUC1 (B). Where indicated 0.4 µg of pRShRXR (Kleiwer et al., *Nature* 358:771–774, 1992) was added. Gemfibrozil or clofibric acid (CFA) were added to a final concentration of 100 µM and 1 mM respectively.

Figure 4:
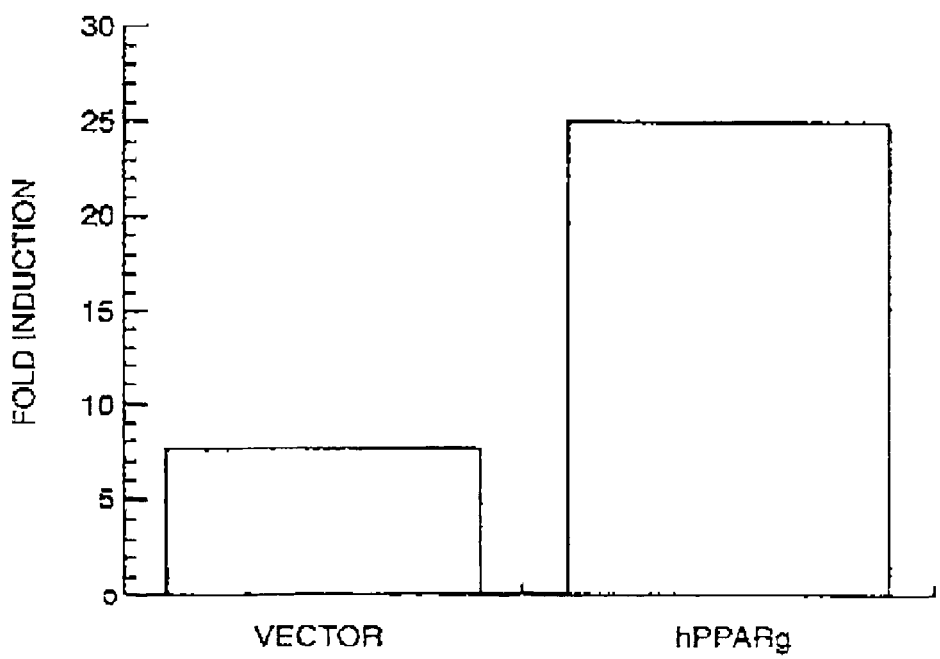

FIG. 4 is a graph showing normalized response of a reporter gene to thiazolidinedione.

CV-1 cells were transfected with pCMVhPPARγ3 or the empty expression vector pBKCMV (no receptor). Thiazolidinedione was added. Fold induction is defined as the ratio of the maximal response observed in the presence of the compound to that in its absence.

In all the figures, hPPARg=hPPARγ, hPPARa=hPPARα, RXRa=RXRα.

DESCRIPTION OF THE PREFERRED EMBODIMENTS

I. Adipocyte Differentiation and PPARγ.

Adipocytes play a central role in lipid homeostasis and the maintenance of energy balance in humans. They function to store and release lipid in response to the metabolic needs of an organism. Pathological conditions associated with adipocyte abnormity include obesity and several lipodystrophy syndromes. Obesity is associated with an increased risk for cardiovascular disease, diabetes and an increased mortality rate (see Grundy et al., *Disease-a-Month* 36:645–696, 1990). Current treatment for obesity includes diet, exercise and surgery (Leibel, R. L. et al., *New England Journal of Medicine* 332:621–628, 1995).

Adipocyte differentiation involves dramatic changes in gene expression. A number of transcription factors have been identified as potential regulators of this process, e.g., CCAATT enhancer-binding protein α (C/EBPα) binds to the promoters of several fat cell genes (Christy et al., *Genes Dev.* 3:1325–1335, 1989), and overexpression of this factor can promote adipogenesis in fibroblastic cell lines (Freytag et al., *Genes Dev.* 8:1654–1663, 1994).

Mouse PPARγ2 has been identified as a key regulator of fat cell enhancers (Tontonoz et al., *Genes &Development* 8:1224–34, 1994, and Tontonoz et al., *Cell* 79:1147–1156, 1994). It is expressed at very high levels specifically in adipose tissue and forms a heterodimer with mouse RXRα to activate the adipocyte-specific enhancer aP2. Forced expression of mouse PPARγ2 in fibroblast cell lines that do not normally differentiate into adipocytes is sufficient to cause overt adipose differentiation of the cell line in the presence of dexamethasone and PPAR activators, suggesting a role in adipose differentiation and lipid metabolism.

II. Cardio-Protective Effect of hPPARα and hPPARγ.

The effect of hypolipidemic drugs like gemfibrozil that have significant cardio-protective effect are mediated via hPPARα. Applicant determined that hPPARγ is a specific repressor of the transcriptional activation effected by hPPARα polypeptide. The repressive action of hPPARγ protein on hPPARα may limit the clinical efficacy of hPPARα agonists (e.g., fibrates). Agents that relieve this repression will increase activity of hPPARα and increase the efficacy of existing drugs, or render these drugs unnecessary because endogenous activators of PPARα can then work with greater efficacy.

Since hPPARγ is shown by Applicant to be present in the human heart, kidney, pancreas, skeletal muscle, and liver tissues where hPPARα is also present, the screening methods of this invention and agents identified thereby may have widespread therapeutic significance.

Applicant has demonstrated co-operative binding of hPPARγ and RXRα, RXRβ or RXRγ to a PPAR response element, PPRE. Without being bound by any particular theory, applicant proposes that repression of hPPARα by hPPARγ likely occurs by sequestering RXRα, thereby antagonizing transcription activation activity of hPPARα protein.

The present invention relates to hPPARγ polypeptides, nucleic acids encoding such polypeptides, cells, tissues and animals containing such nucleic acids, antibodies to such polypeptides, assays utilizing such polypeptides, and methods relating to all of the foregoing. The above mentioned compositions are used to screen for hPPARγ agonists and antagonists, which can be used as lead compounds to designed drugs active on hPPARγ related pathological conditions, such as obesity. The above mentioned compositions are also used to establish cell cultures or animal models to study adipocyte differentiation or obesity in humans.

The invention will now be described in greater detail by reference to the following examples regarding screening for hPPARγ agonists and antagonists. This invention, however, is not limited to co-transfection assay, gel retardation assay and immunoprecipitation assay described below. Other methods known to those skilled in the art for assaying an agent that relieve the repressive effect of a protein on a cellular activity may also be used.

III. Materials and Methods.

Experimental procedures and reagents employed in the examples described herein are set forth below:

Reagents

ETYA, β-estradiol, ATRA, LT3 (3,3',5-triiodo-L-thyronine) and CFA were purchased from Sigma, and WY-14,643 from Chemsyn Science Laboratories, Lenexa, Kans., USA. Stock solutions of these compounds were made in ethanol, methanol or dimethyl sulfoxide (ETYA, LY-171,883 and gemfibrozil in ethanol, 9-cis-retinoic acid in dimethyl sulfoxide).

The recipes for buffers, mediums, and solutions in the following examples are given in J. Sambrook, E. F. Fritsch, and T. Maniatis, *Molecular Cloning: A Laboratory Manual*, 2 Ed., Cold Spring Harbor Laboratory Press, Cold Spring Harbor, N.Y., 1989.

Vector Construction

For mammalian expression studies, the entire hPPARγ cDNA was subcloned into the EcoRI site of pcDNA-1 (Invitrogen, San Diego, Calif.) under the control of the CMV promoter to make plasmid pCMVhPPARγ. The hPPARα cDNA was cloned into the NotI site of pBKCMV (Stratagene) to give pCMVhPPARα. The hNUC1B cDNA was directionally cloned into the SalI-SacII site of pBKCMV to give pCMVhNUC1B.

The reporter plasmid pPPREA3-tk-luc was generated by inserting three copies of the synthetic oligonucleotide (5'-CCCGAACGTGACCTTTGTCCTGGTCC-3') (SEQ ID NO: 7) containing the "A" site of the Acyl-CoA oxidase gene regulatory sequence (Osumi et al., *Biochem. Biophys. Res. Commun.* 175: 866–871, 1991) into the XhoI site 5' of the tk promoter in the previously described pBLtk-luciferase vector (Giguere et al., *Cell* 46: 645–652, 1986).

pRShRARα, pRShRXRα, MTV-TREp2-LUC, and CRB-PII-tk-LUC have been described in Giguere et al., *Nature* 330(2):624–629, 1987; Mangelsdorf et al., *Nature* 345: 224–229, 1990; Umesono et al., *Nature* 336:262–265, 1988 and Mangelsdorf et al., *Cell* 66:555–561, 1991.

Co-transfection Assay

CV-1 or HepG2 cells were grown in Dulbecco's modified Eagle's medium (DMEM) supplemented with 10% (v/v) fetal bovine serum (Hyclone), 2 mM L-glutamine, and 55 μg/ml gentamicin (BioWhittaker). Cells were plated at $2\times10^5$ cells per well for HepG2 in 12 well cell culture dishes (Costar). The media was replaced with fresh media 20 hours later. After 4 hours, DNA was added by the calcium phosphate coprecipitation technique (Berger, T. S., Parandosh, Z., Perry, B., and Stein, R. B. (1992) J. Steroid. Biochem. Molec. Biol. 41, 733–738). Typically, 0.1 μg of expression plasmid, 0.5 μg of the β-gal expression plasmid pCH110 (internal control), and 0.5 mg of reporter plasmid were added to each well.

Where indicated, 0–0.5 μg of hNUC1B plasmid or hPPARγ plasmid (repressor) was added. Repressor plasmid dosage was kept constant by the addition of appropriate amounts of the empty expression vector pBKCMV. Total amount of DNA was kept at 20 μg by the addition of pGEM DNA (Promega).

After 14 hours the cells were washed with 1×PBS and fresh media added (DMEM with 10% charcoal stripped fetal bovine serum (Hyclone) plus the above supplements). Ligands or PPAR activators were added to the final concentrations indicated. Control cells were treated with vehicle.

After another 24 hours the cells were harvested and the luciferase and β-galactosidase activities quantified on a Dynatech ML 1000 luminometer and a Beckman Biomek 1000 workstation respectively. The normalized response is the luciferase activity of the extract divided by the β-galactosidase activity of the same. Each data point represents the mean of three transfections. Error bars represent the standard deviation from the mean. CAT assays were performed as in Ausbel et al., (1987) in *Current Protocols in Molecular Biology*, Wiley Interscience.

Gel Retardation Assay

Gel retardation assays with PPRE sequences were performed as described in Mukherjee et al., *JSBMB* 51: 157–166, 1993, incorporated by reference herein. hPPARγ was translated in vitro using the T3 coupled reticulocyte lysate system (Promega). The baculovirus/Sf21 cell system was used to express hRXRα (Allegretto et al., *JBC* 268: 1–9, 1993, incorporated by reference herein). The sequences of the oligonucleotides containing PPREs from three genes are 5'-CTAGCGATATCATGACCTTTGTCCTAGGCCTC-3' (SEQ ID NO: 3) (acyl coenzyme A oxidase), 5'-GATC-CCTTTGACCTATTGAACTATTACCTACATTA-3' (SEQ ID NO: 4) (hydratase) and 5'-GATCCCCACTGAACCCT-TGACCCCTGCCCTGCAGCA-3' (SEQ ID NO: 5) (human ApoA1 'A' site).

COS cells were transfected with 5 μg of pCMVhNUC1B or pRShRXRα (Ptashne, *Nature* 335:683–689, 1988) per 100 mm dish for 48 hours. Whole cell extracts were made by four cycles of freeze-thawing in 0.4 M KCl containing buffer followed by centrifugation. Gel retardations were performed by incubating 5 μg of cell extract in buffer containing 10 mM Hepes (7.8), 50 mM KCl, 1 mM DTT, 2.5 mM $MgCl_2$, 0.5 mg/ml dIdC and 20% glycerol at 4° C. for 5 minutes. About 100,000 cpm of $^{32}P$-end-labeled probe was then added and incubated at 25° C. for another 5 minutes.

Protein-DNA sequences complexes were resolved by electrophoresis on 5% polyacrylamide gels in 0.5×TBE. The PPRE sequence from the acyl-coenzymeA oxidase (AOX) gene used as probe is 5'-CTAGCGATATCATGAC-CTTTGTCCTAGGCCTC-3'(SEQ ID NO: 3) (upper strand) and 5'-CTAGGAGGCCTAGGACAAAGGTCAT-GATATCG-3' (SEQ ID NO: 6) (lower strand).

IV. cDNA Cloning of hPPARγ and Nucleic Acid Encoding a hPPARγ Polypeptide.

What follows is an example of the cloning of a hPPARγ from a human heart cDNA library. Those of ordinary skill in the art will recognize that equivalent procedures can be readily used to isolate hPPARγ from genomic libraries or cDNA libraries of other tissues.

The recipes for buffers, mediums, and solutions in the following experiments are given in J. Sambrook, E. F. Fritsch, and T. Maniatis, *Molecular Cloning: A Laboratory Manual*, 2 Ed., Cold Spring Harbor Laboratory Press, Cold Spring Harbor, N.Y., 1989.

A human heart cDNA library, Human Heart 5'-STRETCH in λ-gt10, was purchased from Clontech Laboratories Inc., Palo Alto, Calif.

A fragment isolated from a mPPARγ cDNA clone (Chen et al., *Biochem. Biophy. Res. Com.* 196:671–677, 1993) by digestion with EcoRI, was labeled with [$^{32}$P]-dCTP by random priming and was utilized to identify potential hPPARγ cDNA clones.

Approximately 2×10$^6$ phage plaques from the human heart cDNA library were screened with the mPPARγ probe at low stringency (35% formamide, 5×SSC, 0.1% SDS, 100 μg/ml fish DNA at 37° C.). Positive clones were isolated and subcloned into pBKCMV (Strategene) or pCRII (Invitrogen) for sequencing. The hPPARγ clone contains an open reading frame of 1482 nucleotides (see SEQ. ID NO. 1). There is an 89% nucleotide identity (i.e., "homology") between the hPPARγ clone and the mPPARγ sequence.

hPPARγ may start from any of the three methionines identified in SEQ. ID NO. 2, i.e., Met (1), Met (18) and Met (20). The deduced amino acid sequence of hPPARγ predicts a protein of 494, 477 or 475 amino acids. A comparison of the amino acid sequences between human and mouse show 96% amino acid sequence identity (i.e., "homology").

Included within the scope of this invention are the functional equivalents of the herein-described isolated nucleic acid molecules. The degeneracy of the genetic code permits substitution of certain codons by other codons which specify the same amino acid and hence would give rise to the same protein. The nucleic acid sequence can vary substantially since, with the exception of methionine and tryptophan, the known amino acids can be coded for by more than one codon. Thus, portions or all of the hPPARγ gene could be synthesized to give a nucleic acid sequence significantly different from that shown in SEQ ID NO: 1. The encoded amino acid sequence thereof would, however, be preserved.

In addition, the nucleic acid sequence may comprise a nucleotide sequence which results from the addition, deletion or substitution of at least one nucleotide to the 5'-end and/or the 3'-end of the nucleic acid formula shown in SEQ ID NO: 1 or a derivative thereof. Any nucleotide or polynucleotide may be used in this regard, provided that its addition, deletion or substitution does not alter the amino acid sequence of SEQ ID NO:2 which is encoded by the nucleotide sequence. For example, the present invention is intended to include any nucleic acid sequence resulting from the addition of ATG as an initiation codon at the 5'-end of the inventive nucleic acid sequence or its derivative, or from the addition of TTA, TAG or TGA as a termination codon at the 3'-end of the inventive nucleotide sequence or its derivative. Moreover, the nucleic acid molecule of the present invention may, as necessary, have restriction endonuclease recognition sites added to its 5'-end and/or 3'-end.

Such functional alterations of a given nucleic acid sequence afford an opportunity to promote secretion and/or processing of heterologous proteins encoded by foreign nucleic acid sequences fused thereto. All variations of the nucleotide sequence of the hPPARγ genes and fragments thereof permitted by the genetic code are, therefore, included in this invention.

Further, it is possible to delete codons or to substitute one or more codons by codons other than degenerate codons to produce a structurally modified polypeptide, but one which has substantially the same utility or activity of the polypeptide produced by the unmodified nucleic acid molecule. As recognized in the art, the two polypeptides are functionally equivalent, as are the two nucleic acid molecules which give rise to their production, even though the differences between the nucleic acid molecules are not related to degeneracy of the genetic code.

V. Detecting Transcription Pattern of the Three Human PPAR Subtypes in Different Human Tissues with Nucleic Acid Probe.

Northern blots of mRNA from various human tissues were hybridized with human PPAR subtype specific probes to determine the expression pattern of human PPAR subtypes.

A human multiple tissue Northern blot (Clontech Laboratories Inc.) containing 2 μg of poly-A plus mRNA isolated from several human tissues was hybridized with the full length hPPARγ cDNA that had been random prime labeled with [$^{32}$P]-dCTP. The hybridization and all washes were conducted under high-stringency.

The result showed that the three human PPAR subtypes are expressed differently in different human tissues. hPPARα is expressed predominantly in the liver, kidney, heart and skeletal muscle, with lower levels in the pancreas, placenta and lung, and nondetectable in the brain. hNUC1 is ubiquitously expressed in different tissues, with the highest expression levels in the placenta and low levels in the liver. hPPARγ is expressed at the highest levels in the liver, heart and skeletal muscle, with lower levels in the kidney and pancreas, and nondetectable in the brain, placenta, or lung.

A nucleic acid probe of the present invention may be used to probe an appropriate chromosomal or cDNA library by usual hybridization methods to obtain another nucleic acid molecule of the present invention. A chromosomal DNA or cDNA library may be prepared from appropriate cells according to recognized methods in the art (cf. Molecular Cloning: A Laboratory Manual, second edition, edited by Sambrook, Fritsch, & Maniatis, Cold Spring Harbor Laboratory, 1989).

In the alternative, chemical synthesis is carried out in order to obtain nucleic acid probes having nucleotide sequences which correspond to N-terminal and C-terminal portions of the amino acid sequence of the polypeptide of interest. Thus, the synthesized nucleic acid probes may be used as primers in a polymerase chain reaction (PCR) carried out in accordance with recognized PCR techniques, essentially according to PCR Protocols, A Guide to Methods and Applications, edited by Michael et al., Academic Press, 1990, utilizing the appropriate chromosomal or cDNA library to obtain the fragment of the present invention.

One skilled in the art can readily design such probes based on the sequence disclosed herein using methods of computer alignment and sequence analysis known in the art (cf. Molecular Cloning: A Laboratory Manual, second edition, edited by Sambrook, Fritsch, & Maniatis, Cold Spring Harbor Laboratory, 1989). The hybridization probes of the present invention can be labeled by standard labeling techniques such as with a radiolabel, enzyme label, fluorescent label, biotin-avidin label, chemiluminescence, and the like. After hybridization, the probes may be visualized using known methods.

The nucleic acid probes of the present invention include RNA, as well as DNA probes, such probes being generated using techniques known in the art. The nucleic acid probe may be immobilized on a solid support. Examples of such solid supports include, but are not limited to, plastics such as polycarbonate, complex carbohydrates such as agarose and sepharose, and acrylic resins, such as polyacrylamide and latex beads. Techniques for coupling nucleic acid probes to such solid supports are well known in the art.

The test samples suitable for nucleic acid probing methods of the present invention include, for example, cells or nucleic acid extracts of cells, or biological fluids. The sample used in the above-described methods will vary based on the assay format, the detection method and the nature of the tissues, cells or extracts to be assayed. Methods for preparing nucleic acid extracts of cells are well known in the art and can be readily adapted in order to obtain a sample which is compatible with the method utilized.

One method of detecting the presence of hPPARγ in a sample comprises a) contacting said sample with the above-described nucleic acid probe, under conditions such that hybridization occurs, and b) detecting the presence of said probe bound to said nucleic acid molecule. One skilled in the art would select the nucleic acid probe according to techniques known in the art as described above. Samples to be tested include but should not be limited to RNA samples of human tissue.

A kit for detecting the presence of hPPARγ in a sample comprises at least one container means having disposed therein the above-described nucleic acid probe. The kit may further comprise other containers comprising one or more of the following: wash reagents and reagents capable of detecting the presence of bound nucleic acid probe. Examples of detection reagents include, but are not limited to radiolabelled probes, enzymatic labeled probes (horse radish peroxidase, alkaline phosphatase), and affinity labeled probes (biotin, avidin, or steptavidin).

In detail, a compartmentalized kit includes any kit in which reagents are contained in separate containers. Such containers include small glass containers, plastic containers or strips of plastic or paper. Such containers allow the efficient transfer of reagents from one compartment to another compartment such that the samples and reagents are not cross-contaminated and the agents or solutions of each container can be added in a quantitative fashion from one compartment to another. Such containers will include a container which will accept the test sample, a container which contains the probe or primers used in the assay, containers which contain wash reagents (such as phosphate buffered saline, Tris-buffers, and the like), and containers which contain the reagents used to detect the hybridized probe, bound antibody, amplified product, or the like. One skilled in the art will readily recognize that the nucleic acid probes described in the present invention can readily be incorporated into one of the established kit formats which are well known in the art.

VI. Expression of Recombinant hPPARγ Polypeptide with DNA Constructs Containing a hPPARγ Polypeptide Encoding Sequence.

Applicant expressed recombinant hPPARγ in vitro. One predominant band estimated to be about 50 kd was observed. This is compatible with translation initiation at the third ATG codon from the 5'-end (position 214, SEQ. I.D. No. 1). A lower band is observed in the in vitro translated hPPARγ polypeptides, which could be a degraded hPPARγ polypeptide or a hPPARγ polypeptide translation from an internal methionine.

Amino acid sequence comparison of hPPARγ with other PPAR subtypes shows that human PPARγ has 96% identity to mPPARγ1 and 55% identity to both hPPARα and hNUC. The closest homology among PPAR subtypes is in the DNA binding domains, followed by the ligand binding domains. The N-terminal A/B domain, which in the PPAR family encodes a transactivation function, is very different in the three human PPAR subtypes, suggesting that these human PPAR subtypes may have different transactivation properties.

The present invention also relates to a recombinant DNA molecule comprising, 5' to 3', a promoter effective to initiate transcription in a host cell and the above-described nucleic acid molecules. In addition, the present invention relates to a recombinant DNA molecule comprising a vector and an above-described nucleic acid molecules. The present invention also relates to a nucleic acid molecule comprising a transcriptional region functional in a cell, a sequence complimentary to an RNA sequence encoding an amino acid sequence corresponding to the above-described polypeptide, and a transcriptional termination region functional in said cell. The above-described molecules may be isolated and/or purified DNA molecules.

The present invention also relates to a cell or organism that contains an above-described nucleic acid molecule. The peptide may be purified from cells which have been altered to express the peptide. A cell is said to be "altered to express a desired peptide" when the cell, through genetic manipulation, is made to produce a protein which it normally does not produce or which the cell normally produces at lower levels. One skilled in the art can readily adapt procedures for introducing and expressing either genomic, cDNA, or synthetic sequences into either eukaryotic or prokaryotic cells.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene sequence expression. The precise nature of the regulatory regions needed for gene sequence expression may vary from organism to organism, but shall in general include a promoter region which, in prokaryotes, contains both the promoter (which directs the initiation of RNA transcription) as well as the DNA sequences which, when transcribed into RNA, will signal synthesis initiation. Such regions will normally include those 5'-non-coding sequences involved with initiation of transcription and translation, such as the TATA box, capping sequence, CAAT sequence, and the like.

If desired, the non-coding region 3' to the sequence encoding an hPPAR-γ gene may be obtained by the above-described methods. This region may be retained for its transcriptional termination regulatory sequences, such as termination and polyadenylation. Thus, by retaining the 3'-region naturally contiguous to the DNA sequence encoding an hPPARγ gene, the transcriptional termination signals may be provided. Where the transcriptional termination signals are not satisfactorily functional in the expression host cell, then a 3' region functional in the host cell may be substituted.

Two DNA sequences (such as a promoter region sequence and a hPPARγ sequence) are said to be operably linked if the nature of the linkage between the two DNA sequences does not (1) result in the introduction of a frame-shift mutation, (2) interfere with the ability of the promoter region sequence to direct the transcription of a hPPARγ gene sequence, or (3) interfere with the ability of a hPPARγ gene sequence to be transcribed by the promoter region sequence. Thus, a promoter region would be operably linked to a DNA sequence if the promoter were capable of effecting transcription of that DNA sequence. Thus, to express a hPPARγ gene, transcriptional and translational signals recognized by an appropriate host are necessary.

The present invention encompasses the expression of the hPPARγ gene (or a functional derivative thereof) in either prokaryotic or eukaryotic cells. Prokaryotic hosts are, generally, very efficient and convenient for the production of recombinant proteins and are, therefore, one type of preferred expression system for the hPPARγ gene. Prokaryotes most frequently are represented by various strains of *E. coli*. However, other microbial strains may also be used, including other bacterial strains.

In prokaryotic systems, plasmid vectors that contain replication sites and control sequences derived from a species compatible with the host may be used. Examples of suitable plasmid vectors may include pBR322, pUC118, pUC119 and the like; suitable phage or bacteriophage vectors may include λgt10, λgt11 and the like; and suitable virus vectors may include pMAM-neo, pKRC and the like. Preferably, the selected vector of the present invention has the capacity to replicate in the selected host cell.

Recognized prokaryotic hosts include bacteria such as *E. coli, Bacillus, Streptomyces, Pseudomonas, Salmonella, Serratia*, and the like. However, under such conditions, the peptide will not be glycosylated. The prokaryotic host must be compatible with the replicon and control sequences in the expression plasmid.

To express hPPARγ (or a functional derivative thereof) in a prokaryotic cell, it is necessary to operably link the hPPARγ sequence to a functional prokaryotic promoter. Such promoters may be either constitutive or, more preferably, regulatable (i.e., inducible or derepressible). Examples of constitutive promoters include the int promoter of bacteriophage λ, the bla promoter of the β-lactamase gene sequence of pBR322, and the CAT promoter of the chloramphenicol acetyl transferase gene sequence of pPR325, and the like. Examples of inducible prokaryotic promoters include the major right and left promoters of bacteriophage λ ($P_L$ and $P_R$), the trp, recA, lacZ, lacI, and gal promoters of *E. coli*, the α-amylase (Ulmanen et at., J. Bacteriol. 162: 176–182(1985)) and the ς-28-specific promoters of *B. subtilis* (Gilman et at., Gene sequence 32:11–20(1984)), the promoters of the bacteriophages of *Bacillus* (Gryczan, In: The Molecular Biology of the Bacilli, Academic Press, Inc., NY (1982)), and *Streptomyces* promoters (Ward et at., Mol. Gen. Genet. 203:468–478(1986)). Prokaryotic promoters are reviewed by Glick (J. Ind. Microbiot. 1:277–282(1987)); Cenatiempo (Biochimie 68:505–516(1986)); and Gottesman (Ann. Rev. Genet. 18:415–442 (1984)).

Proper expression in a prokaryotic cell also requires the presence of a ribosome binding site upstream of the gene sequence-encoding sequence. Such ribosome binding sites are disclosed, for example, by Gold et al. *Ann. Rev. Microbiol.* 35:365–404(1981). The selection of control sequences, expression vectors, transformation methods, and the like, are dependent on the type of host cell used to express the gene. As used herein, "cell", "cell line", and "cell culture" may be used interchangeably and all such designations include progeny. Thus, the words "transformants" or "transformed cells" include the primary subject cell and cultures derived therefrom, without regard to the number of transfers. It is also understood that all progeny may not be precisely identical in DNA content, due to deliberate or inadvertent mutations. However, as defined, mutant progeny have the same functionality as that of the originally transformed cell.

Host cells which may be used in the expression systems of the present invention are not strictly limited, provided that they are suitable for use in the expression of the hPPARγ polypeptide of interest. Suitable hosts may often include eukaryotic cells. Preferred eukaryotic hosts include, for example, yeast, fungi, insect cells, mammalian cells either in vivo, or in tissue culture. Mammalian cells which may be useful as hosts include HeLa cells, cells of fibroblast origin such as VERO or CHO-K1, or cells of lymphoid origin and their derivatives. Preferred mammalian host cells include SP2/0 and J558L, as well as neuroblastoma cell lines such as IMR 332 which may provide better capacities for correct post-translational processing.

In addition, plant cells are also available as hosts, and control sequences compatible with plant cells are available, such as the cauliflower mosaic virus 35S and 19S, and nopaline synthase promoter and polyadenylation signal sequences. Another preferred host is an insect cell, for example the *Drosophila* larvae. Using insect cells as hosts, the *Drosophila* alcohol dehydrogenase promoter can be used. Rubin, Science 240:1453–1459(1988). Alternatively, baculovirus vectors can be engineered to express large amounts of hPPARγ in insects cells (Jasny, Science 238: 1653 (1987); Miller et al., In: Genetic Engineering (1986), Setlow, J. K., et al., eds., Plenum, Vol. 8, pp. 277–297).

Any of a series of yeast gene sequence expression systems can be utilized which incorporate promoter and termination elements from the actively expressed gene sequences coding for glycolytic enzymes are produced in large quantities when yeast are grown in mediums rich in glucose. Known glycolytic gene sequences can also provide very efficient transcriptional control signals. Yeast provides substantial advantages in that it can also carry out post-translational peptide modifications. A number of recombinant DNA strategies exist which utilize strong promoter sequences and high copy number of plasmids which can be utilized for production of the desired proteins in yeast. Yeast recognizes leader sequences on cloned mammalian gene sequence products and secretes peptides bearing leader sequences (i.e., prepeptides). For a mammalian host, several possible vector systems are available for the expression of hPPARγ.

A wide variety of transcriptional and translational regulatory sequences may be employed, depending upon the nature of the host. The transcriptional and translational regulatory signals may be derived from viral sources, such as adenovirus, bovine papilloma virus, cytomegalovirus, simian virus, or the like, where the regulatory signals are associated with a particular gene sequence which has a high level of expression. Alternatively, promoters from mammalian expression products, such as actin, collagen, myosin, and the like, may be employed. Transcriptional initiation regulatory signals may be selected which allow for repression or activation, so that expression of the gene sequences can be modulated. Of interest are regulatory signals which are temperature-sensitive so that by varying the temperature, expression can be repressed or initiated, or are subject to chemical (such as metabolite) regulation.

Expression of hPPARγ in eukaryotic hosts requires the use of eukaryotic regulatory regions. Such regions will, in general, include a promoter region sufficient to direct the initiation of RNA synthesis. Preferred eukaryotic promoters include, for example, the promoter of the mouse metallothionein I gene sequence (Hamer et al., J. Mol. Appl. Gen. 1:273–288(1982)); the TK promoter of Herpes virus (McKnight, Cell 31:355–365 (1982)); the SV40 early promoter (Benoist et al., Nature (London) 290:304–310(1981)); the yeast gal4 gene sequence promoter (Johnston et al., Proc. Natl. Acad. Sci. (USA) 79:6971–6975(1982); Silver et al., Proc. Natl. Acad. Sci. (USA) 81:5951–5955 (1984)).

Translation of eukaryotic mRNA is initiated at the codon which encodes the first methionine. For this reason, it is preferable to ensure that the linkage between a eukaryotic promoter and a DNA sequence which encodes hPPARγ (or a functional derivative thereof) does not contain any intervening codons which are capable of encoding a methionine (i.e., AUG). The presence of such codons results either in a formation of a fusion protein (if the AUG codon is in the same reading frame as the hPPARγ coding sequence) or a frame-shift mutation (if the AUG codon is not in the same reading frame as the hPPARγ coding sequence).

A hPPARγ nucleic acid molecule and an operably linked promoter may be introduced into a recipient prokaryotic or eukaryotic cell either as a nonreplicating DNA (or RNA) molecule, which may either be a linear molecule or, more preferably, a closed covalent circular molecule. Since such molecules are incapable of autonomous replication, the expression of the gene may occur through the transient expression of the introduced sequence. Alternatively, permanent expression may occur through the integration of the introduced DNA sequence into the host chromosome.

A vector may be employed which is capable of integrating the desired gene sequences into the host cell chromosome. Cells which have stably integrated the introduced DNA into their chromosomes can be selected by also introducing one or more markers which allow for selection of host cells which contain the expression vector. The marker may provide for prototrophy to an auxotrophic host, biocide resistance, e.g., antibiotics, or heavy metals, such as copper, or the like. The selectable marker gene sequence can either be directly linked to the DNA gene sequences to be expressed, or introduced into the same cell by co-transfection. Additional elements may also be needed for optimal synthesis of single chain binding protein mRNA. These elements may include splice signals, as well as transcription promoters, enhancers, and termination signals. cDNA expression vectors incorporating such elements include those described by Okayama, Molec. Cell. Biol. 3:280(1983).

The introduced nucleic acid molecule can be incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species. Preferred prokaryotic vectors include plasmids such as those capable of replication in *E. coli* (such as, for example, pBR322, ColEl, pSC101, PACYC 184, πVX. Such plasmids are, for example, disclosed by Sambrook (cf. Molecular Cloning: A Laboratory Manual, second edition, edited by Sambrook, Fritsch, & Maniatis, Cold Spring Harbor Laboratory, (1989)). *Bacillus* plasmids include pC194, pC221, pT127, and the like. Such plasmids are disclosed by Gryczan (In: The Molecular Biology of the Bacilli, Academic Press, NY (1982), pp. 307–329). Suitable *Streptomyces* plasmids include p1J101 (Kendall et al., J. Bacteriol. 169:4177–4183 (1987)), and *streptomyces* bacteriophages such as ΦC31 (Chater et al., In: Sixth International Symposium on Actinomycetales Biology, Akademiai Kaido, Budapest, Hungary (1986), pp. 45–54). *Pseudomonas* plasmids are reviewed by John et al. (Rev. Infect. Dis. 8:693–704(1986)), and Izaki (Jpn. J. Bacteriol. 33:729–742 (1978)).

Preferred eukaryotic plasmids include, for example, BPV, vaccinia, SV40, 2-micron circle, and the like, or their derivatives. Such plasmids are well known in the art (Botstein et al., Miami Wntr. Symp. 19:265–274(1982)); Broach, In: The Molecular Biology of the Yeast *Saccharomyces*: Life Cycle and Inheritance, Cold Spring Harbor Laboratory, Cold Spring Harbor, N.Y., p. 445–470 (1981); Broach, Cell 28:203–204 (1982); Bollon et at., J. Ctin. Hematol. Oncol. 10:39–48 (1980); Maniatis, In: Cell Biology: A Comprehensive Treatise, Vol. 3, Gene Sequence Expression, Academic Press, NY, pp. 563–608(1980).

Once the vector or nucleic acid molecule containing the construct(s) has been prepared for expression, the DNA construct(s) may be introduced into an appropriate host cell by any of a variety of suitable means, i.e., transformation, transfection, conjugation, protoplast fusion, electroporation, particle gun technology, calcium phosphate-precipitation, direct microinjection, and the like. After the introduction of the vector, recipient cells are grown in a selective medium, which selects for the growth of vector-containing cells. Expression of the cloned gene molecule(s) results in the production of hPPARγ or fragments thereof. This can take place in the transformed cells as such, or following the induction of these cells to differentiate (for example, by administration of bromodeoxyuracil to neuroblastoma cells or the like). A variety of incubation conditions can be used to form the peptide of the present invention. The most preferred conditions are those which mimic physiological conditions.

VII. hPPARγ Polypeptides, Antibody and Hybridoma.

A variety of methodologies known in the art can be utilized to obtain the peptide of the present invention. The peptide may be purified from tissues or cells which naturally produce the peptide. Alternatively, the above-described isolated nucleic acid fragments could be used to expressed the hPPARγ protein in any organism. The samples of the present invention include cells, protein extracts or membrane extracts of cells, or biological fluids. The sample will vary based on the assay format, the detection method and the nature of the tissues, cells or extracts used as the sample.

Any eukaryotic organism can be used as a source for the peptide of the invention, as long as the source organism naturally contains such a peptide. As used herein, "source organism" refers to the original organism from which the amino acid sequence of the subunit is derived, regardless of the organism the subunit is expressed in and ultimately isolated from.

One skilled in the art can readily follow known methods for isolating proteins in order to obtain the peptide free of natural contaminants. These include, but are not limited to: size-exclusion chromatography, HPLC, ion-exchange chromatography, and immuno-affinity chromatography.

The present invention relates to an antibody having binding affinity to a hPPARγ polypeptide. The polypeptide may have the amino acid sequence set forth in SEQ ID NO:2, or mutant or species variation thereof, or at least 9 contiguous amino acids thereof (preferably, at least 10, 15, 20, or 30 contiguous amino acids thereof).

The present invention also relates to an antibody having specific binding affinity to an hPPARγ polypeptide. Such an antibody may be isolated by comparing its binding affinity to a hPPARγ polypeptide with its binding affinity to another polypeptide. Those which bind selectively to hPPARγ would be chosen for use in methods requiring a distinction between hPPARγ and other polypeptides.

The hPPARγ proteins of the present invention can be used in a variety of procedures and methods, such as for the generation of antibodies, for use in identifying pharmaceutical compositions, and for studying DNA/protein interaction.

The hPPARγ peptide of the present invention can be used to produce antibodies or hybridomas. One skilled in the art will recognize that if an antibody is desired, such a peptide would be generated as described herein and used as an immunogen. The antibodies of the present invention include monoclonal and polyclonal antibodies, as well fragments of these antibodies, and humanized forms. Humanized forms of the antibodies of the present invention may be generated using one of the procedures known in the art such as chimerization or CDR grafting. The present invention also relates to a hybridoma which produces the above-described monoclonal antibody, or binding fragment thereof. A hybridoma is an immortalized cell line which is capable of secreting a specific monoclonal antibody.

In general, techniques for preparing monoclonal antibodies and hybridomas are well known in the art (Campbell, "Monoclonal Antibody Technology: Laboratory Techniques in Biochemistry and Molecular Biology," Elsevier Science Publishers, Amsterdam, The Netherlands (1984); St. Groth et al., J. Immunol. Methods 35:1–21(1980)). Any animal (mouse, rabbit, and the like) which is known to produce antibodies can be immunized with the selected polypeptide. Methods for immunization are well known in the art. Such methods include subcutaneous or intraperitoneal injection of the polypeptide. One skilled in the art will recognize that the amount of polypeptide used for immunization will vary based on the animal which is immunized, the antigenicity of the polypeptide and the site of injection.

The polypeptide may be modified or administered in an adjuvant in order to increase the peptide antigenicity. Methods of increasing the antigenicity of a polypeptide are well known in the art. Such procedures include coupling the antigen with a heterologous protein (such as globulin or β-galactosidase) or through the inclusion of an adjuvant during immunization.

For monoclonal antibodies, spleen cells from the immunized animals are removed, fused with myeloma cells, such as SP2/0-Ag14 myeloma cells, and allowed to become monoclonal antibody producing hybridoma cells. Any one of a number of methods well known in the art can be used to identify the hybridoma cell which produces an antibody with the desired characteristics. These include screening the hybridomas with an ELISA assay, western blot analysis, or radioimmunoassay (Lutz et al., Exp. Cell Res. 175:109–124 (1988)). Hybridomas secreting the desired antibodies are cloned and the class and subclass is determined using procedures known in the art (Campbell, Monoclonal Antibody Technology: Laboratory Techniques in Biochemistry and Molecular Biology, supra (1984)).

For polyclonal antibodies, antibody containing antisera is isolated from the immunized animal and is screened for the presence of antibodies with the desired specificity using one of the above-described procedures. The above-described antibodies may be detectably labeled. Antibodies can be detectably labeled through the use of radioisotopes, affinity labels (such as biotin, avidin, and the like), enzymatic labels (such as horse radish peroxidase, alkaline phosphatase, and the like) fluorescent labels (such as FITC or rhodamine, and the like), paramagnetic atoms, and the like. Procedures for accomplishing such labeling are well-known in the art, for example, see (Sternberger et al., J. Histochem. Cytochem. 18:315(1970); Bayer et at., Meth. Enzym. 62:308(1979); Engval et al., Immunot. 109:129(1972); Goding, J. Immunol. Meth. 13:215(1976)). The labeled antibodies of the present invention can be used for in vitro, in vivo, and in situ assays to identify cells or tissues which express a specific peptide.

The above-described antibodies may also be immobilized on a solid support. Examples of such solid supports include plastics such as polycarbonate, complex carbohydrates such as agarose and sepharose, acrylic resins and such as polyacrylamide and latex beads. Techniques for coupling antibodies to such solid supports are well known in the art (Weir et al., "Handbook of Experimental Immunology" 4th Ed., Blackwell Scientific Publications, Oxford, England, Chapter 10(1986); Jacoby et al., Meth. Enzym. 34 Academic Press, N.Y. (1974)). The immobilized antibodies of the present invention can be used for in vitro, in vivo, and in situ assays as well as in immunochromotography.

Furthermore, one skilled in the art can readily adapt currently available procedures, as well as the techniques, methods and kits disclosed above with regard to antibodies, to generate peptides capable of binding to a specific peptide sequence in order to generate rationally designed antipeptide peptides, for example see Hurby et al., "Application of Synthetic Peptides: Antisense Peptides", In Synthetic Peptides, A User's Guide, W.H. Freeman, NY, pp. 289–307 (1992), and Kaspczak et al., Biochemistry 28:9230–8(1989).

Anti-peptide peptides can be generated by replacing the basic amino acid residues found in the hPPARγ peptide sequence with acidic residues, while maintaining hydrophobic and uncharged polar groups. For example, lysine, arginine, and/or histidine residues are replaced with aspartic acid or glutamic acid and glutamic acid residues are replaced by lysine, arginine or histidine.

The present invention encompasses a method of detecting a hPPARγ polypeptide in a sample, comprising: a) contacting the sample with an above-described antibody, under conditions such that immunocomplexes form, and b) detecting the presence of said antibody bound to the polypeptide. In detail, the methods comprise incubating a test sample with one or more of the antibodies of the present invention and assaying whether the antibody binds to the test sample.

Conditions for incubating an antibody with a test sample vary. Incubation conditions depend on the format employed in the assay, the detection methods employed, and the type and nature of the antibody used in the assay. One skilled in the art will recognize that any one of the commonly available immunological assay formats (such as radioimmunoassays, enzyme-linked immunosorbent assays, diffusion based Ouchterlony, or rocket immunofluorescent assays) can readily be adapted to employ the antibodies of the present invention. Examples of such assays can be found in Chard, "An Introduction to Radioimmunoassay and Related Techniques" Elsevier Science Publishers, Amsterdam, The Netherlands (1986); Bullock et al., "Techniques in Immunocytochemistry," Academic Press, Orlando, Fla. Vol. 1(1982), Vol. 2 (1983), Vol. 3 (1985); Tijssen, "Practice and Theory of Enzyme Immunoassays: Laboratory Techniques in Biochemistry and Molecular Biology," Elsevier Science Publishers, Amsterdam, The Netherlands (1985).

The immunological assay test samples of the present invention include cells, protein or membrane extracts of cells, or biological fluids such as blood, serum, plasma, or urine. The test sample used in the above-described method will vary based on the assay format, nature of the detection method and the tissues, cells or extracts used as the sample to be assayed. Methods for preparing protein extracts or membrane extracts of cells are well known in the art and can be readily be adapted in order to obtain a sample which is capable with the system utilized.

A kit contains all the necessary reagents to carry out the previously described methods of detection. The kit may comprise: i) a first container means containing an above-described antibody, and ii) second container means containing a conjugate comprising a binding partner of the antibody and a label. In another preferred embodiment, the kit further comprises one or more other containers comprising one or more of the following: wash reagents and reagents capable of detecting the presence of bound antibodies.

Examples of detection reagents include, but are not limited to, labeled secondary antibodies, or in the alternative, if the primary antibody is labeled, the chromophoric, enzymatic, or antibody binding reagents which are capable of reacting with the labeled antibody. The compartmentalized kit may be as described above for nucleic acid probe kits. One skilled in the art will readily recognize that the antibodies described in the present invention can readily be incorporated into one of the established kit formats which are well known in the art.

VIII. Transgenic Animals Containing a hPPARγ Encoding Sequence and Gene Therapy.

A variety of methods are available for the production of transgenic animals associated with this invention. DNA can be injected into the pronucleus of a fertilized egg before fusion of the male and female pronuclei, or injected into the nucleus of an embryonic cell (e.g., the nucleus of a two-cell embryo) following the initiation of cell division (Brinster et al., *Proc. Nat. Acad. Sci. USA* 82: 4438–4442 (1985)). Embryos can be infected with viruses, especially retroviruses, modified to carry inorganic-ion receptor nucleotide sequences of the invention.

Pluripotent stem cells derived from the inner cell mass of the embryo and stabilized in culture can be manipulated in culture to incorporate nucleotide sequences of the invention. A transgenic animal can be produced from such cells through implantation into a blastocyst that is implanted into a foster mother and allowed to come to term. Animals suitable for transgenic experiments can be obtained from standard commercial sources such as Charles River (Wilmington, Mass.), Taconic (Germantown, N.Y.), Harlan Sprague Dawley (Indianapolis, Ind.), etc.

The procedures for manipulation of the rodent embryo and for microinjection of DNA into the pronucleus of the zygote are well known to those of ordinary skill in the art (Hogan et al., supra). Microinjection procedures for fish, amphibian eggs and birds are detailed in Houdebine and Chourrout, *Experientia* 47: 897–905 (1991). Other procedures for introduction of DNA into tissues of animals are described in U.S. Pat. No., 4,945,050 (Sandford et al., Jul. 30, 1990).

By way of example only, to prepare a transgenic mouse, female mice are induced to superovulate. Females are placed with males, and the mated females are sacrificed by $CO_2$ asphyxiation or cervical dislocation and embryos are recovered from excised oviducts. Surrounding cumulus cells are removed. Pronuclear embryos are then washed and stored until the time of injection. Randomly cycling adult female mice are paired with vasectomized males. Recipient females are mated at the same time as donor females. Embryos then are transferred surgically. The procedure for generating transgenic rats is similar to that of mice. See Hammer et al., *Cell* 63:1099–1112 (1990).

Methods for the culturing of embryonic stem (ES) cells and the subsequent production of transgenic animals by the introduction of DNA into ES cells using methods such as electroporation, calcium phosphate/DNA precipitation and direct injection also are well known to those of ordinary skill in the art. See, for example, *Teratocarcinomas and Embryonic Stem Cells, A Practical Approach*, E. J. Robertson, ed., IRL Press (1987).

In cases involving random gene integration, a clone containing the sequence(s) of the invention is co-transfected with a gene encoding resistance. Alternatively, the gene encoding neomycin resistance is physically linked to the sequence(s) of the invention. Transfection and isolation of desired clones are carried out by any one of several methods well known to those of ordinary skill in the art (E. J. Robertson, supra).

DNA molecules introduced into ES cells can also be integrated into the chromosome through the process of homologous recombination. Capecchi, *Science* 244: 1288–1292 (1989). Methods for positive selection of the recombination event (i.e., neo resistance) and dual positive-negative selection (i.e., neo resistance and gancyclovir resistance) and the subsequent identification of the desired clones by PCR have been described by Capecchi, supra and Joyner et al., *Nature* 338: 153–156 (1989), the teachings of which are incorporated herein. The final phase of the procedure is to inject targeted ES cells into blastocysts and to transfer the blastocysts into pseudopregnant females. The resulting chimeric animals are bred and the offspring are analyzed by Southern blotting to identify individuals that carry the transgene. Procedures for the production of non-rodent mammals and other animals have been discussed by others. See Houdebine and Chourrout, supra; Pursel et al., *Science* 244:1281–1288 (1989); and Simms et al., *Bio/Technology* 6:179–183 (1988).

hPPARγ or its genetic sequences will be useful in gene therapy (reviewed in Miller, *Nature* 357:455–460, (1992). Miller states that advances have resulted in practical approaches to human gene therapy that have demonstrated positive initial results. An in vivo model of gene therapy for human severe combined immunodeficiency is described in Ferrari, et al., *Science* 251:1363–1366, (1991). The basic science of gene therapy is described in Mulligan, *Science* 260:926–931, (1993).

In one preferred embodiment, an expression vector containing the hPPARγ coding sequence is inserted into cells, the cells are grown in vitro and then infused in large numbers into patients. In another preferred embodiment, a DNA segment containing a promoter of choice (for example a strong promoter) is transferred into cells containing an endogenous hPPARγ in such a manner that the promoter segment enhances expression of the endogenous hPPARγ gene (for example, the promoter segment is transferred to the cell such that it becomes directly linked to the endogenous hPPARγ gene).

The gene therapy may involve the use of an adenovirus containing hPPARγ cDNA targeted to a tumor, systemic hPPARγ increase by implantation of engineered cells, injection with hPPARγ virus, or injection of naked hPPARγ DNA into appropriate tissues.

Target cell populations (e.g., hematopoietic or nerve cells) may be modified by introducing altered forms of hPPARγ in order to modulate the activity of such cells.

Expression vectors derived from viruses such as retroviruses, vaccinia virus, adenovirus, adeno-associated virus, herpes viruses, several RNA viruses, or bovine papilloma virus, may be used for delivery of nucleotide sequences (e.g., cDNA) encoding recombinant hPPARγ protein into the targeted cell population (e.g., tumor cells). Methods which are well known to those skilled in the art can be used to construct recombinant viral vectors containing coding sequences. See, for example, the techniques described in Maniatis et al., *Molecular Cloning: A Laboratory Manual*, Cold Spring Harbor Laboratory, N.Y. (1989), and in Ausubel et al., *Current Protocols in Molecular Biology*, Greene Publishing Associates and Wiley Interscience, N.Y. (1989). Alternatively, recombinant nucleic acid molecules encoding protein sequences can be used as naked DNA or in reconstituted system e.g., liposomes or other lipid systems for delivery to target cells (See e.g., Felgner et al., *Nature* 337:387–8, 1989). Several other methods for the direct transfer of plasmid DNA into cells exist for use in human gene therapy and involve targeting the DNA to receptors on cells by complexing the plasmid DNA to proteins. See, Miller, supra.

In its simplest form, gene transfer can be performed by simply injecting minute amounts of DNA into the nucleus of a cell, through a process of microinjection. Capecchi MR, *Cell* 22:479–88 (1980). Once recombinant genes are introduced into a cell, they can be recognized by the cell's normal mechanisms for transcription and translation, and a gene product will be expressed. Other methods have also been attempted for introducing DNA into larger numbers of cells. These methods include: transfection, wherein DNA is precipitated with $CaPO_4$ and taken into cells by pinocytosis (Chen C. and Okayama H, *Mol. Cell Biol.* 7:2745–52 (1987)); electroporation, wherein cells are exposed to large voltage pulses to introduce holes into the membrane (Chu G. et al., *Nucleic Acids Res.,* 15:1311–26 (1987)); lipofection/liposome fusion, wherein DNA is packaged into lipophilic vesicles which fuse with a target cell (Felgner PL., et al., *Proc. Natl. Acad. Sci. USA.* 84:7413–7 (1987)); and particle bombardment using DNA bound to small projectiles (Yang NS. et al., *Proc. Natl. Acad. Sci.* 87:9568–72 (1990)). Another method for introducing DNA into cells is to couple the DNA to chemically modified proteins.

It has also been shown that adenovirus proteins are capable of destabilizing endosomes and enhancing the uptake of DNA into cells. The admixture of adenovirus to solutions containing DNA complexes, or the binding of DNA to polylysine covalently attached to adenovirus using protein crosslinking agents substantially improves the uptake and expression of the recombinant gene. Curiel DT et al., *Am. J. Respir. Cell. Mol. Biol.,* 6:247–52 (1992).

As used herein "gene transfer" means the process of introducing a foreign nucleic acid molecule into a cell. Gene transfer is commonly performed to enable the expression of a particular product encoded by the gene. The product may include a protein, polypeptide, anti-sense DNA or RNA, or enzymatically active RNA. Gene transfer can be performed in cultured cells or by direct administration into animals. Generally gene transfer involves the process of nucleic acid contact with a target cell by non-specific or receptor mediated interactions, uptake of nucleic acid into the cell through the membrane or by endocytosis, and release of nucleic acid into the cytoplasm from the plasma membrane or endosome. Expression may require, in addition, movement of the nucleic acid into the nucleus of the cell and binding to appropriate nuclear factors for transcription.

As used herein "gene therapy" is a form of gene transfer and is included within the definition of gene transfer as used herein and specifically refers to gene transfer to express a therapeutic product from a cell in vivo or in vitro. Gene transfer can be performed ex vivo on cells which are then transplanted into a patient, or can be performed by direct administration of the nucleic acid or nucleic acid-protein complex into the patient.

In another preferred embodiment, a vector having nucleic acid sequences encoding hPPARγ is provided in which the nucleic acid sequence is expressed only in specific tissue. Methods of achieving tissue-specific gene expression as set forth in International Publication No. WO 93/09236, filed Nov. 3, 1992 and published May 13, 1993.

In all of the preceding vectors set forth above, a further aspect of the invention is that the nucleic acid sequence contained in the vector may include additions, deletions or modifications to some or all of the sequence of the nucleic acid, as defined above.

In another preferred embodiment, a method of gene replacement is set forth. "Gene replacement" as used herein means supplying a nucleic acid sequence which is capable of being expressed in vivo in an animal and thereby providing or augmenting the function of an endogenous gene which is missing or defective in the animal.

IX. Isolation of Agonists and Antagonists of hPPARγ.

The present invention also relates to a method of detecting an agonist or antagonist of hPPARγ polypeptide comprising incubating cells that produce hPPARγ polypeptide in the presence of a compound and detecting changes in the level of hPPARγ activity. Standard techniques can be used, including, but not limited to, what is described in Evans et al., U.S. Pat. No. 5,071,773, Beaumont et al., U.S. Pat. No. 5,264,372, PCT application PCT/US94/03795 (publication no. WO 94/23068) and U.S. application Ser. No. 08/270,635 entitled "Screening for NUC inhibitors," by Mukherjee, incorporated by reference herein.

Figure 1:
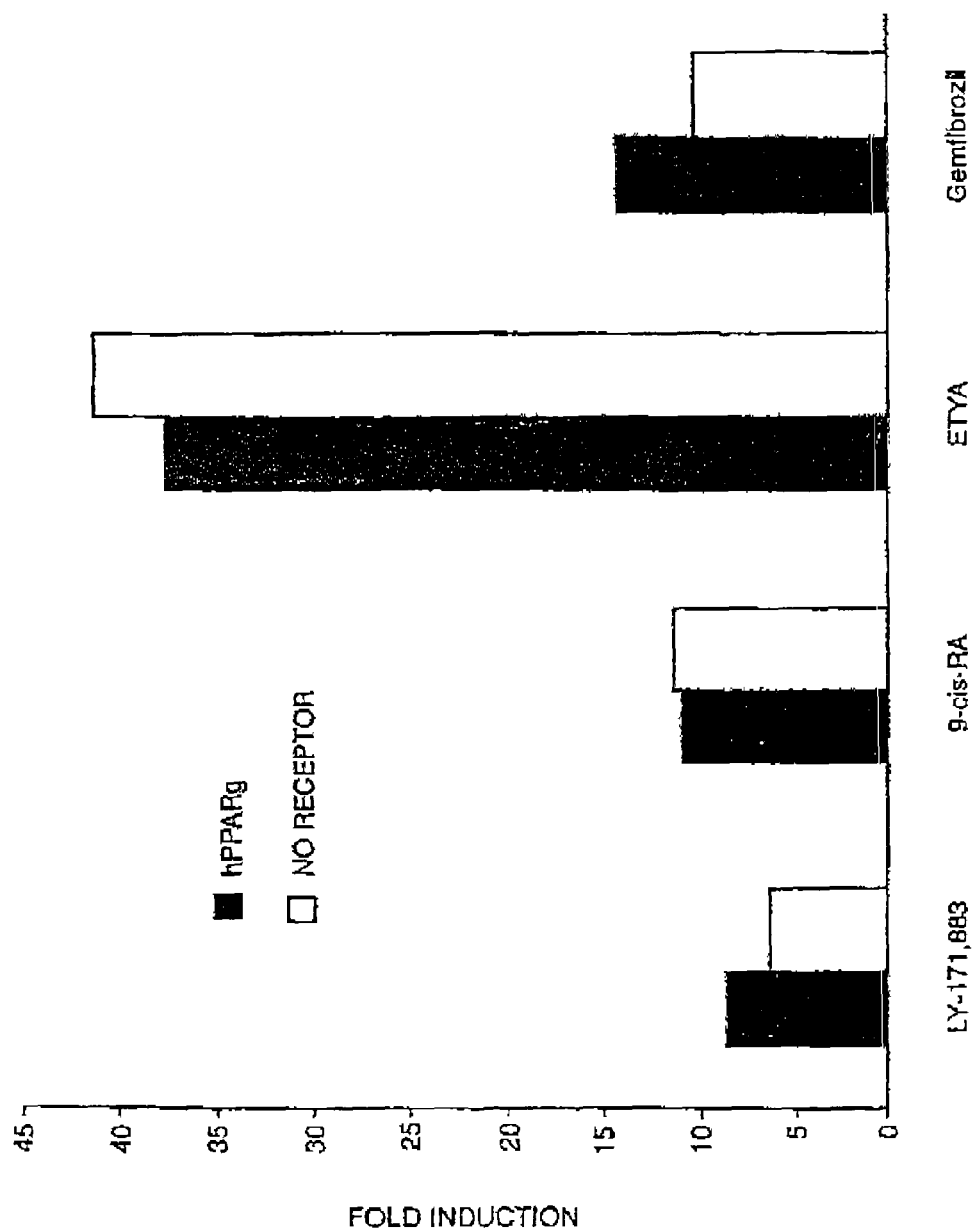
FIG. 1 is a graph showing induction of hPPARγ by various compounds.

Various compounds were tested for their ability to transactivate hPPARγ (FIG. 1). LY-171,883 and gemfibrozil showed marginal activation of hPPARγ above that seen in control cells. ETYA or 9-cis retinoic acid showed the same fold activation as in control transfections. Thus the response of hPPARγ to LY-171,883 and ETYA is different from that seen with mPPARγ, which is transcriptionally activated by these compounds (Tontonoz et al., *Genes and Devel.* 8:1224–1234, 1994; Tontonoz et al., *Cell* 79:1147–1156, 1994; and Kliewer et al., *PNAS* 91:7355–7359).

To increase the level of hPPARγ protein synthesis, Applicant deleted a region containing the two inframe upstream ATG codons since these are absent in mouse PPARγ. pCM-VhPPARγ was digested with NcoI, blunt ended with Klenow, and digested again with KpnI. The insert was isolated and directionally cloned into pBKCMV plasmid, which was digested with XbaI (blunt ended with Klenow) and KpnI. In the ensuing plasmid pCMVhPPARγ3, the translation initiation codon is within the context of a stronger Kozak translation initiation sequence.

A cotransfection assay was performed in CV-1 cells with the pPREA3-tk-LUC and 1 μM thiazolidinedione (BRL 49,653, see Ibrahimi et al., *Molecular Pharmacology* 46:1070–1076, 1994). Thiazolidinedione is an insulin sensitizer and has potential use in the treatment of non-insulin dependant diabetes mellitus.

Thiazolidinedione activated hPPARγ (FIG. 4). In cells transfected with pCMVhPPARγ3, 25 fold induction was observed in the presence of the compound while only 7 fold activation was seen in cells transfected with the empty expression vector.

The present invention also encompasses a method of agonizing (stimulating) or antagonizing hPPARγ associated activity in a mammal comprising administering to said mammal an agonist or antagonist to hPPARγ in an amount sufficient to effect said agonism or antagonism.

X. Screening for hPPARγ Inhibitors.

Co-transfection assay shows that hPPARγ polypeptides repress the activity of hPPARα. Applicant uses the following screening method to identify compounds that derepress the activity of hPPARα.

hPPARα is activated in the presence of gemfibrozil. When hNUC1 or hPPARγ is contransfected into cells along with hPPARα, a dose dependant repression was observed (FIG. 2). Repression of hPPARα with hNUC1 is stronger than with hPPARγ. No repression with 0.1 µg of hPPARγ was observed while repression with 0.1 µg of hNUC1 was clearly seen. However, repression with 0.4 µg of hPPARγ was observed. Using equal amounts of transfected receptor, higher levels of repression was observed with hNUC1 compared to hPPARγ.

hPPARγ and hNUC1 repress hPPARα transcription by sequestering RXR. The repression of hPPARα activity by 0.4 µg of hPPARγ (FIG. 3A) or 0.1 µg of hNUC1 (FIG. 3B) was overcome by cotransfecting 0.4 µg of an RXRα expression plasmid. Repression by hPPARγ was completely overcome. However, relief of repression was intermediate in the case of hNUC1. This suggests that hNUC1 is a stronger repressor than hPPARγ. The mere presence of excess RXR in the cell is sufficient to relieve repression.

Compounds were dissolved in ethanol (ETYA, LY-171, 883 and gemfibrozil) or DMSO (9-cis-retinoic acid). Control cells received an equivalent amount of vehicle. In the repression assays repressor plasmid dosage was kept constant by adding the appropriate amount of the empty expression vector pBKCMV.

Applicant has determined that hPPARγ is a specific repressor of the transcriptional activation effected by PPARα. The repressive action of hPPARγ on PPARα may limit the clinical efficacy of PPARα activators (e.g., fibrates, synthroid). Agents that relieve this repression will increase activity of PPARα increase the efficacy of existing drugs, or render these drugs unnecessary.

Applicant has demonstrated co-operative binding of hPPARγ and RXRα to a PPAR response element, PPRE. Without being bound by any particular theory, applicant proposes that hPPARγ polypeptides repress PPARα by sequestering RXR or competing for DNA binding.

Screening for hPPARγ Inhibitors with Co-transfection Assay

In order to screen for agents that relieve the repression PPARα activity by hPPARγ, PPARα and hPPARγ expressing plasmids will be contransfected into CV-1 (a monkey kidney cell line) or HepG2 (a human liver cell line) cells along with a reporter containing PPAR binding elements (such as PPREs) in the presence of a PPAR activator (e.g., clofibiric acid, WY-14,643) or a TR activator (e.g., LT3).

Clofibric acid or LT3 normally activate their respective receptors and will therefore give a strong signal. In the presence of hPPARγ the signal will be very weak because of repression of these receptors by hNUC1B. We will add compounds to the transfected cells at various concentrations and select those that relieve the repression by hPPARγ.

The above screening strategy will also be followed in a yeast based assay with appropriate vectors and reporters.

Screening for hPPARγ Inhibitors by Gel Retardation Assay

Gel retardation assays showed that hPPARγ binds to a PPAR element, PPRE, with hRXRα.

Gel shift assays performed with in vitro translated hPPARγ polypeptides and recombinant baculovirus expressed RXRα polypeptides showed that hPPARγ binds to PPREs as a heterodimer with RXRα. hPPARγ alone did not form a complex with oligonucleotides containing PPRE sequences from the Acyl CoenzymeA oxidase (Mukherjee et al., *JSBMB* 51:157–166, 1994), bifunctional enzyme (Zhang et al., *JBC* 268:12939–12945, 1993) or the A site of the human ApoA1 gene promoters. However, a strong retarded complex was formed when both hPPARγ and RXRα were present with oligo containing PPRE sequences. No retarded complex was observed with RXRα alone. Retarded complexes were also observed when hPPARγ was mixed with mRXRβ or mRXRγ.

XI. Pharmaceutical Formulations and Modes of Administration.

The particular compound or antibody that affects the disorder of interest can be administered to a patient either by themselves, or in pharmaceutical compositions where it is mixed with suitable carriers or excipient(s). In treating a patient exhibiting a disorder of interest, a therapeutically effective amount of a agent or agents such as these is administered. A therapeutically effective dose refers to that amount of the compound that results in amelioration of symptoms or a prolongation of survival in a patient.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized.

For any compound used in the method of the invention, the therapeutically effective dose can be estimated initially from cell culture assays. For example, a dose can be formulated in animal models to achieve a circulating plasma concentration range that includes the $IC_{50}$ as determined in cell culture (i.e., the concentration of the test compound which achieves a half-maximal disruption of the protein complex, or a half-maximal inhibition of the cellular level and/or activity of a complex component). Such information can be used to more accurately determine useful doses in humans. Levels in plasma may be measured, for example, by HPLC.

The exact formulation, route of administration and dosage can be chosen by the individual physician in view of the patient's condition. (See e.g. Fingl et al., in *The Pharmacological Basis of Therapeutics,* 1975, Ch. 1 p. 1). It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administrated dose in the management of the oncogenic disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Depending on the specific conditions being treated, such agents may be formulated and administered systemically or locally. Techniques for formulation and administration may be found in *Remington's Pharmaceutical Sciences,* 18th ed., Mack Publishing Co., Easton, Pa. (1990). Suitable routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few.

For injection, the agents of the invention may be formulated in aqueous solutions, preferably in physiologically compatible buffers such as Hanks's solution, Ringer's solution, or physiological saline buffer. For such transmucosal administration, penetrants appropriate to the barrier to be permeated are used in the formulation. Such penetrants are generally known in the art.

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Agents intended to be administered intracellularly may be administered using techniques well known to those of ordinary skill in the art. For example, such agents may be encapsulated into liposomes, then administered as described above. Liposomes are spherical lipid bilayers with aqueous interiors. All molecules present in an aqueous solution at the time of liposome formation are incorporated into the aqueous interior. The liposomal contents are both protected from the external microenvironment and, because liposomes fuse with cell membranes, are efficiently delivered into the cell cytoplasm. Additionally, due to their hydrophobicity, small organic molecules may be directly administered intracellularly.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein. In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions. The pharmaceutical compositions of the present invention may be manufactured in a manner that is itself known, e.g., by means of conventional mixing, dissolving, granulating, dragee-making, levitating, emulsifying, encapsulating, entrapping or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

Some methods of delivery that may be used include:
a. encapsulation in liposomes,
b. transduction by retroviral vectors,
c. localization to nuclear compartment utilizing nuclear targeting site found on most nuclear proteins,
d. transfection of cells ex vivo with subsequent reimplantation or administration of the transfected cells,
e. a DNA transporter system.

A hPPARγ nucleic acid sequence may be administered utilizing an ex vivo approach whereby cells are removed from an animal, transduced with the hPPARγ nucleic acid sequence and reimplanted into the animal. The liver can be accessed by an ex vivo approach by removing hepatocytes from an animal, transducing the hepatocytes in vitro with the hPPARγ nucleic acid sequence and reimplanting them into the animal (e.g., as described for rabbits by Chowdhury et al, *Science* 254: 1802–1805, 1991, or in humans by Wilson, *Hum. Gene Ther.* 3: 179–222, 1992) incorporated herein by reference.

Many nonviral techniques for the delivery of a hPPARγ nucleic acid sequence into a cell can be used, including direct naked DNA uptake (e.g., Wolff et al., *Science* 247:

1465–1468, 1990), receptor-mediated DNA uptake, e.g., using DNA coupled to asialoorosomucoid which is taken up by the asialoglycoprotein receptor in the liver (Wu and Wu, *J. Biol. Chem.* 262: 4429–4432, 1987; Wu et al., *J. Biol. Chem.* 266: 14338–14342, 1991), and liposome-mediated delivery (e.g., Kaneda et al., *Expt. Cell Res.* 173: 56–69, 1987; Kaneda et al., *Science* 243: 375–378, 1989; Zhu et al., *Science* 261: 209–211, 1993). Many of these physical methods can be combined with one another and with viral techniques; enhancement of receptor-mediated DNA uptake can be effected, for example, by combining its use with adenovirus (Curiel et al., *Proc. Natl. Acad. Sci. USA* 88: 8850–8854, 1991; Cristiano et al., *Proc. Natl. Acad. Sci. USA* 90: 2122–2126, 1993).

The hPPARγ or nucleic acid encoding hPPARγ may also be administered via an implanted device that provides a support for growing cells. Thus, the cells may remain in the implanted device and still provide the useful and therapeutic agents of the present invention.

All publications referenced are incorporated by reference herein, including the nucleic acid sequences and amino acid sequences listed in each publication.

Other embodiments are within the following claims.

What is claimed is:

1. An isolated nucleic acid comprising a contiguous nucleic acid sequence encoding SEQ ID NO: 2 and an operably linked promoter.

2. The nucleic acid of claim 1, wherein the contiguous nucleic acid sequence consists of nucleotide 157 to 1641 of SEQ ID NO: 1 or its fully complementary strand of the same length.

3. An isolated nucleic acid comprising a contiguous nucleic acid sequence encoding amino acid residue 18 to 494 of SEQ ID NO: 2 and an operably linked promoter.

4. The nucleic acid of claim 3, wherein the contiguous nucleic acid sequence consists of nucleotide 208 to 1641 of SEQ ID NO: 1 or its fully complementary strand of the same length.

5. An isolated nucleic acid comprising a contiguous nucleic acid sequence encoding amino acid residue 20 to 494 of SEQ ID NO: 2 and an operably linked promoter.

6. The nucleic acid of claim 5, wherein the contiguous nucleic acid sequence consists of nucleotide 214 to 1641 of SEQ ID NO: 1 or its fully complementary strand of the same length.

7. An isolated nucleic acid comprising a contiguous nucleic acid sequence encoding SEQ ID NO: 2.

8. The nucleic acid of claim 7, wherein the contiguous nucleic acid sequence consists of nucleotide 157 to 1641 of SEQ ID NO: 1 or its fully complementary strand of the same length.

9. An isolated nucleic acid comprising a contiguous nucleic acid sequence encoding amino acid residue 18 to 494 of SEQ ID NO: 2.

10. The nucleic acid of claim 9, wherein the contiguous nucleic acid sequence consists of nucleotide 208 to 1641 of SEQ ID NO: 1 or its fully complementary strand of the same length.

11. An isolated nucleic acid comprising a contiguous nucleic acid sequence encoding amino acid residue 20 to 494 of SEQ ID NO: 2.

12. The nucleic acid of claim 11, wherein the contiguous nucleic acid sequence consists of nucleotide 214 to 1641 of SEQ ID NO: 1 or its fully complementary strand of the same length.

13. The nucleic acid of claim 1, wherein the nucleic acid is a recombinant nucleic acid.

14. The nucleic acid of claim 2, wherein the nucleic acid is a recombinant nucleic acid.

15. The nucleic acid of claim 3, wherein the nucleic acid is a recombinant nucleic acid.

16. The nucleic acid of claim 4, wherein the nucleic acid is a recombinant nucleic acid.

17. The nucleic acid of claim 5, wherein the nucleic acid is a recombinant nucleic acid.

18. The nucleic acid of claim 6, wherein the nucleic acid is a recombinant nucleic acid.

19. The nucleic acid of claim 7, wherein the nucleic acid is a recombinant nucleic acid.

20. The nucleic acid of claim 8, wherein the nucleic acid is a recombinant nucleic acid.

21. The nucleic acid of claim 9, wherein the nucleic acid is a recombinant nucleic acid.

22. The nucleic acid of claim 10, wherein the nucleic acid is a recombinant nucleic acid.

23. The nucleic acid of claim 11, wherein the nucleic acid is a recombinant nucleic acid.

24. The nucleic acid of claim 12, wherein the nucleic acid is a recombinant nucleic acid.

25. A purified or enriched nucleic acid comprising a contiguous nucleic acid sequence encoding SEQ ID NO: 2.

26. The nucleic acid of claim 25, wherein the contiguous nucleic acid sequence consists of nucleotide 157 to 1641 of SEQ ID NO: 1 or its fully complementary strand of the same length.

27. A purified or enriched nucleic acid comprising a contiguous nucleic acid sequence encoding amino acid residue 18 to 494 of SEQ ID NO: 2.

28. The nucleic acid of claim 27, wherein the contiguous nucleic acid sequence consists of nucleotide 208 to 1641 of SEQ ID NO: 1 or its fully complementary strand of the same length.

29. A purified or enriched nucleic acid comprising a contiguous nucleic acid sequence encoding amino acid residue 20 to 494 of SEQ ID NO: 2.

30. The nucleic acid of claim 29, wherein the contiguous nucleic acid sequence consists of nucleotide 214 to 1641 of SEQ ID NO: 1 or its fully complementary strand of the same length.

31. The nucleic acid of claim 25, further comprising a promoter operably linked to the contiguous nucleic acid sequence.

32. The nucleic acid of claim 26, further comprising a promoter operably linked to the contiguous nucleic acid sequence.

33. The nucleic acid of claim 27, further comprising a promoter operably linked to the contiguous nucleic acid sequence.

34. The nucleic acid of claim 28, further comprising a promoter operably linked to the contiguous nucleic acid sequence.

35. The nucleic acid of claim 29, further comprising a promoter operably linked to the contiguous nucleic acid sequence.

36. The nucleic acid of claim 30, further comprising a promoter operably linked to the contiguous nucleic acid sequence.

* * * * *

UNITED STATES PATENT AND TRADEMARK OFFICE
CERTIFICATE OF CORRECTION

PATENT NO. : 7,115,728 B1 Page 1 of 1
APPLICATION NO. : 08/484487
DATED : October 3, 2006
INVENTOR(S) : Ranjan Mukherjee It is certified that error appears in the above-identified patent and that said Letters Patent is hereby corrected as shown below:

IN THE TITLE PAGES:
Item [56] References Cited, in OTHER PUBLICATIONS:
in Aperlo, C., et al., please replace "Peroxiosme" with --Peroxisome--
in Kiyoto, please replace 'Adipogenisis" with --Adipogenesis--
in Leibel, et al., please replace "Chenges" with --Changes--
in Salazar-Olivo, please replace "Adipogenisis" with --Adipogenesis--
in Willson, et al., please replace "Anithyperglycemic" with --Antihyperglycemic--
in Derwent Abstract for JP 05 194 209A, plesae replace "cholor" with --chloro--
in Chemical Abstracts Accession No. 123:281583, please replace "Adipogensis" with --Adipogenesis--
in Freytag et al., please replace "progamin" with --program in--
in Jow, L. and R. Mukherjee, please replace "NUC1represses" with --NUC1 represses--
in St. Groth, S.F. and D. Scheidegger, please replace "Scheideggar" with --Scheidegger--
in Ullmann's Encyclopedia of Industrial Chemistry, please replace "Germany)" with --Germany--

Signed and Sealed this

Sixteenth Day of January, 2007

JON W. DUDAS
*Director of the United States Patent and Trademark Office*